(12) United States Patent
Nagayoshi et al.

(10) Patent No.: US 11,574,554 B2
(45) Date of Patent: Feb. 7, 2023

(54) GOAL MANAGEMENT SYSTEM AND NON-TRANSITORY COMPUTER-READABLE STORAGE MEDIUM STORING GOAL MANAGEMENT PROGRAM

(71) Applicants: OMRON HEALTHCARE Co., Ltd., Kyoto (JP); OMRON Corporation, Kyoto (JP)

(72) Inventors: Sho Nagayoshi, Kyoto (JP); Hiroshi Koshimizu, Kyoto (JP); Ken Miyagawa, Kyoto (JP); Keiichi Obayashi, Kyoto (JP)

(73) Assignees: OMRON HEALTHCARE CO., LTD., Kyoto (JP); OMRON CORPORATION, Kyoto (JP)

( * ) Notice: Subject to any disclaimer, the term of this patent is extended or adjusted under 35 U.S.C. 154(b) by 368 days.

(21) Appl. No.: 16/851,383

(22) Filed: Apr. 17, 2020

(65) Prior Publication Data
US 2020/0242963 A1 Jul. 30, 2020

Related U.S. Application Data

(63) Continuation of application No. PCT/JP2018/039024, filed on Oct. 19, 2018.

(30) Foreign Application Priority Data

Oct. 26, 2017 (JP) .............................. JP2017-207221
Oct. 26, 2017 (JP) .............................. JP2017-207222

(51) Int. Cl.
*G09B 19/00* (2006.01)
*G06F 40/20* (2020.01)
(Continued)

(52) U.S. Cl.
CPC ............. *G09B 19/00* (2013.01); *G06F 40/20* (2020.01); *G09B 5/065* (2013.01); *G16H 40/67* (2018.01)

(58) Field of Classification Search
None
See application file for complete search history.

(56) References Cited

U.S. PATENT DOCUMENTS 7,222,066 B1 * 5/2007 Oon ..................... G09B 19/04
704/7
7,885,844 B1 * 2/2011 Cohen .................... G06Q 10/10
(Continued)

FOREIGN PATENT DOCUMENTS

JP     2003016193 A     1/2003
JP     2003-288417 A    10/2003
(Continued)

OTHER PUBLICATIONS

International Preliminary Report on Patentability (Chapter II) of the International Preliminary Examining Authority for PCT/JP2018/039024 with search date of Apr. 4, 2019.
(Continued)

*Primary Examiner* — Paul A D'Agostino
(74) *Attorney, Agent, or Firm* — Birch, Stewart, Kolasch & Birch, LLP

(57) ABSTRACT

A goal management system receives input of a qualitative first goal related to a body of a user (step S111), identifies a quantitative second goal related to the body of the user from the first goal thus received (step S112 to step S117), and presents the second goal thus identified (step S118). The first goal is converted into the quantitative goal for at least one of a plurality of feature amounts related to the body, thereby identifying the second goal including at least one goal obtained by such conversion. The first goal is converted into the quantitative goal for each feature amount corresponding
(Continued)

to a meaning obtained by linguistic analysis. When there are a plurality of meanings obtained by linguistic analysis of the first goal, the first goal is converted into the quantitative goal for each feature amount on the basis of a range of each feature amount per meaning. This makes it possible to indicate a quantitative goal related to the body without receiving input of a goal that is a quantitative numerical value related to the body.

4 Claims, 24 Drawing Sheets

(51) Int. Cl.
*G16H 40/67* (2018.01)
*G09B 5/06* (2006.01)

(56) References Cited

U.S. PATENT DOCUMENTS

| | | | | |
|---|---|---|---|---|
| 8,628,331 | B1* | 1/2014 | Wright | G09B 7/02 |
| | | | | 434/323 |
| 2003/0229529 | A1* | 12/2003 | Mui | G06Q 50/2057 |
| | | | | 705/328 |
| 2007/0106797 | A1* | 5/2007 | Travostino | H04L 41/00 |
| | | | | 709/226 |
| 2007/0150330 | A1* | 6/2007 | McGoveran | G06Q 30/0201 |
| | | | | 705/7.29 |
| 2010/0099954 | A1* | 4/2010 | Dickinson | G09B 19/00 |
| | | | | 600/300 |
| 2010/0262526 | A1* | 10/2010 | Johnson | G06Q 40/06 |
| | | | | 709/227 |
| 2011/0218407 | A1 | 9/2011 | Haberman et al. | |
| 2013/0332394 | A1* | 12/2013 | Greene | G06Q 40/06 |
| | | | | 705/36 R |
| 2014/0106318 | A1* | 4/2014 | Wright | G09B 5/00 |
| | | | | 434/219 |
| 2014/0113263 | A1* | 4/2014 | Jarrell | G09B 23/28 |
| | | | | 434/262 |
| 2015/0037771 | A1* | 2/2015 | Kaleal, III | G16H 50/30 |
| | | | | 434/257 |
| 2015/0066602 | A1* | 3/2015 | Windsor | G06Q 10/06393 |
| | | | | 705/7.39 |
| 2015/0120317 | A1* | 4/2015 | Mayou | G09B 19/00 |
| | | | | 705/2 |
| 2015/0216413 | A1* | 8/2015 | Soyao | H04L 67/12 |
| | | | | 709/204 |
| 2015/0254597 | A1* | 9/2015 | Jahagirdar | G06Q 10/063118 |
| | | | | 705/7.15 |
| 2015/0294595 | A1* | 10/2015 | Hu | G06Q 10/101 |
| | | | | 434/236 |
| 2018/0197434 | A1* | 7/2018 | Kan | H04L 51/046 |

FOREIGN PATENT DOCUMENTS

| | | |
|---|---|---|
| JP | 2006-301766 A | 11/2006 |
| JP | 2008-27293 A | 2/2008 |
| JP | 2008-262504 A | 10/2008 |
| JP | 2009-211134 A | 9/2009 |
| JP | 2010-26958 A | 2/2010 |
| JP | 2013-522730 A | 6/2013 |
| JP | 2014183867 A | 10/2014 |

OTHER PUBLICATIONS

English translation of International Preliminary Report on Patentability (Chapter II) of the International Preliminary Examining Authority for PCT/JP2018/039024 with search date of Apr. 4, 2019.
Japanese Notice of Grounds of Rejection for Japanese Application No. 2017-207222, dated Nov. 30, 2021, with an English translation.
International Search Report of the International Searching Authority for PCT/JP2018/039024 dated Jan. 22, 2019.
Translation of the International Search Report of the International Searching Authority for PCT/JP2018/039024 dated Jan. 22, 2019.

* cited by examiner

| SHARP DAD | = | SHARP | + | DAD |

| AGE | BMI | BODY FAT PERCENTAGE | MUSCLE MASS PERCENTAGE |
|---|---|---|---|
| 10s | 22 | 15 | 45 |
| 20s | 22 | 15 | 40 |
| 30s | 23 | 16 | 36 |
| 40s | 24 | 18 | 33 |
| 50s | 24 | 18 | 30 |
| 60s | 23.5 | 20 | 28 |

| AGE | BMI | BODY FAT PERCENTAGE | MUSCLE MASS PERCENTAGE |
|---|---|---|---|
| 10s | 22 | 15 | 45 |
| 20s | 22 | 15 | 40 |
| 30s | 23 | 16 | 36 |
| 40s | 24 | 18 | 33 |
| 50s | 24 | 18 | 30 |
| 60s | 23.5 | 20 | 28 |

| AGE | CLASSIFICATION (1) | BMI | BODY FAT PERCENTAGE | MUSCLE MASS PERCENTAGE |
|---|---|---|---|---|
| 40s | MODEL-ORIENTED | 17 | 10 | 28 |
| 40s | SPORTS-ORIENTED | 23.5 | 5 | 50 |
| 40s | HEALTH-ORIENTED | 21.5 | 13 | 35 |
| 40s | AVERAGE-ORIENTED | 22 | 15 | 34 |

| AGE | CLASSIFICATION (1) | CLASSIFICATION (2) | BMI | BODY FAT PERCENTAGE | MUSCLE MASS PERCENTAGE | CHEST MEASUREMENT | WAIST MEASUREMENT |
|---|---|---|---|---|---|---|---|
| 40s | MODEL-ORIENTED | SLICK | 17.2 | 9.9 | 30 | 87.5 | 81.2 |
| 40s | MODEL-ORIENTED | STYLISH | 17.4 | 10.4 | 28 | 88.2 | 82.4 |
| 40s | MODEL-ORIENTED | SLENDER | 16.4 | 9.7 | 26 | 85 | 78.8 |
| 40s | SPORTS-ORIENTED | MUSCULAR | 23.8 | 4.5 | 51 | 102.4 | 92.2 |
| 40s | SPORTS-ORIENTED | GOOD PHYSIQUE | 23.7 | 5.5 | 53 | 100.2 | 88 |
| 40s | SPORTS-ORIENTED | BUFF | 23 | 5 | 46 | 104 | 90.2 |
| 40s | HEALTH-ORIENTED | WELL-KEPT PHYSICAL CONDITION | 21.6 | 13.3 | 35 | 97.8 | 85.5 |
| 40s | HEALTH-ORIENTED | ROBUST (COLD-RESISTANT) | 21.4 | 13.1 | 36 | 96.4 | 86.2 |
| 40s | HEALTH-ORIENTED | HEALTHY | 21.5 | 12.6 | 34 | 97 | 85.6 |
| 40s | AVERAGE-ORIENTED | GENERAL | 22 | 15 | 33 | 95.2 | 85.2 |
| 40s | AVERAGE-ORIENTED | ORDINARY | 22 | 14.9 | 34 | 95.2 | 85.4 |
| 40s | AVERAGE-ORIENTED | REASONABLE | 22.1 | 15.2 | 33 | 96.5 | 86 |

FIG. 22

MEANING ANALYSIS OF WORDS SPECIFYING TIME

GOAL MANAGEMENT SYSTEM AND NON-TRANSITORY COMPUTER-READABLE STORAGE MEDIUM STORING GOAL MANAGEMENT PROGRAM

CROSS-REFERENCE TO RELATED APPLICATIONS

This is a continuation of International Application 2017-207221, with an international filing date of Oct. 26, 2017, and International Application 2017-207222 with an international filing date of Oct. 26, 2017 and also International Application, PCT/JP2018/039024, with an international filing date of Oct. 19, 2018 and filed by applicant, the disclosure of which is hereby incorporated by reference in its entirety.

TECHNICAL FIELD

This disclosure relates to a goal management system and a non-transitory computer-readable storage medium storing a goal management program. In particular, the disclosure relates to a goal management system and a non-transitory computer-readable storage medium storing a goal management program suitable for managing a goal related to a body of a user.

BACKGROUND ART

In the related art, there are systems configured to manage a goal related to a body of a user. In such a system, a quantitative numerical value input by the user is used as the goal (refer to, for example, FIG. 4 and the like of JP 2008-262504 A (hereinafter referred to as "Patent Document 1")).

CITATION LIST

Patent Literature

Patent Document 1: JP 2008-262504 A
Patent Document 2: JP 2013-522730 A

SUMMARY OF INVENTION

Technical Problem

However, according to the system of Patent Document 1, the user needs to accurately grasp the current numerical value and the like related to his or her body, appropriately ascertain an achievable goal, and determine the quantitative numerical value, on his or her own.

An object of an aspect of this disclosure is to provide a goal management system and a non-transitory computer-readable storage medium storing a goal management program capable of indicating a quantitative goal related to a body without receiving input of a goal of a quantitative numerical value related to the body.

Solution to Problem

A goal management system according to an aspect of this disclosure includes: a reception unit, an identification unit, and a presentation unit. The reception unit is configured to receive input of a first goal that is qualitative and related to a body of a user. The identification unit is configured to identify a second goal that is quantitative and related to the body of the user, from the first goal received by the reception unit. The presentation unit is configured to present the second goal identified by the identification unit.

The identification unit is configured to convert the first goal into a quantitative goal for at least one feature amount related to the body and corresponding to a meaning obtained by linguistic analysis of the first goal, thereby identifying the second goal including at least one goal obtained by such conversion.

The quantitative goal is a range or a value included in a range of values of a feature amount corresponding to the meaning obtained by linguistic analysis of the first goal. Further, when there are a plurality of meanings obtained by linguistic analysis of the first goal, the quantitative goal is a range or a value included in a range of values of a feature amount per meaning.

Further, when there are a plurality of feature amounts corresponding to a meaning obtained by linguistic analysis of the first goal and there is an overlap in range of the plurality of feature amounts per meaning in a multidimensional space with each of the plurality of feature amounts serving as an axis, the quantitative goal is a value or a range of each feature amount corresponding to a position or a range of a multidimensional space included in the overlapping range.

Preferably, an acquisition unit, a storage unit, a creation unit, and a presentation unit are further included. The acquisition unit is configured to acquire a current value of a predetermined indicator related to the body of the user; and an achievement deadline of a goal. The storage unit is configured to store in advance, in association with a plurality of human attributes, information indicating a trend in goal attainment that is indicated by a combination of a plurality of paths, each path being a transition in value of the predetermined indicator to a goal value for achieving a goal related to a body of a person, and a goal attainment rate per path. The creation unit is configured to create a path having the goal attainment rate higher than those of other paths on the basis of the current value, the second goal, and the achievement deadline, using a trend indicated by information stored in the storage unit. The presentation unit is configured to present the path created by the creation unit.

More preferably, the storage unit is configured to further store a plurality of past goals, each related to a body of a person, in association with the trend. The creation unit is configured to create the path using a trend indicated by, from among the information stored in the storage unit, information of each person having a goal at or near that of the user.

More preferably, the creation unit is configured to create the path using a trend indicated by, from among the information stored in the storage unit, information of each person having an attribute at or near that of the user.

More preferably, the storage unit is configured to store an achievement rate of a goal as the trend. The creation unit is configured to create the path using an achievement rate indicated by, from among the information stored in the storage unit, information of each person having an attribute at or near that of the user.

A goal management program according to another aspect of this disclosure is executed by a control unit of a server including the control unit and the storage unit. The storage unit is configured to store a plurality of types of feature amounts in advance. The control unit executes the goal management program including the steps of: receiving a first goal that is qualitative, related to a body of a user, and received by a terminal device; identifying a second goal that is quantitative and related to the body of the user from the first goal thus received; and transmitting the second goal thus identified to the terminal device for presentation by the terminal device.

Preferably, the server further includes a storage unit configured to store in advance, in association with a plurality of human attributes, information indicating a trend in goal attainment that is indicated by a combination of a plurality of paths, each path being a transition in value of the predetermined indicator to a goal value for achieving a goal related to a body of a person, and a goal attainment rate per path. The server executes the goal management program further including the steps of: acquiring a current value of a predetermined indicator related to the body of the user, the goal value, and an achievement deadline of the goal; creating a path having the goal attainment rate higher than those of other paths from the current value, the goal value, and the achievement deadline thus acquired, using a trend indicated by information stored in the storage unit; and transmitting the path thus created to the terminal device for presentation by the terminal device.

Advantageous Effects of Invention

According to this disclosure, it is possible to provide a goal management system and a non-transitory computer-readable storage medium storing a goal management program capable of indicating a quantitative goal related to a body without receiving input of a goal of a quantitative numerical value related to the body.

BRIEF DESCRIPTION OF DRAWINGS

FIG. 22 shows an example of the database after data accumulation of the values of indicators related to the body composition of an "ideal" person in this embodiment.

DESCRIPTION OF EMBODIMENTS

Embodiments of a goal management system will be described below with reference to the diagrams. In the following description, like parts and components are given like numerals. Names and functions thereof are also the same. Accordingly, the descriptions of such parts and components are not repeated.

Concept

"To improve a habit" means to change one's daily life, which had been considered "normal", to a desirable state and to recognize that desirable daily life as "normal" thereafter. The steps for realizing an improvement of a habit are as follows: (1) Identify the state of a "future" as a desirable normal. (2) Understand what changes are required from the normal that existed "until now". (3) Thoroughly execute a small change that is not a burden to oneself. (4) Recognize the attained "future" desirable state as the new normal for oneself.

Figure 1:
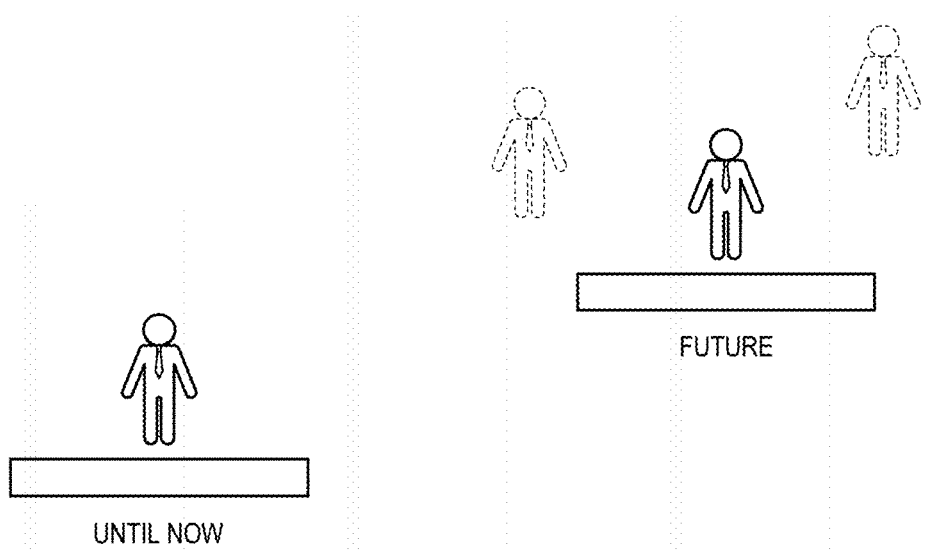
FIG. 1 is a diagram illustrating step 1 for improving a habit.

FIG. 1 to FIG. 9 are diagrams illustrating step 1 through step 9 for improving a habit, respectively. With reference to FIG. 1, in step 1, a value is converted into a numerical value. That is, once a desired body shape is decided, a numerical goal of a predetermined indicator required for the realization is clearly defined.

Figure 2:
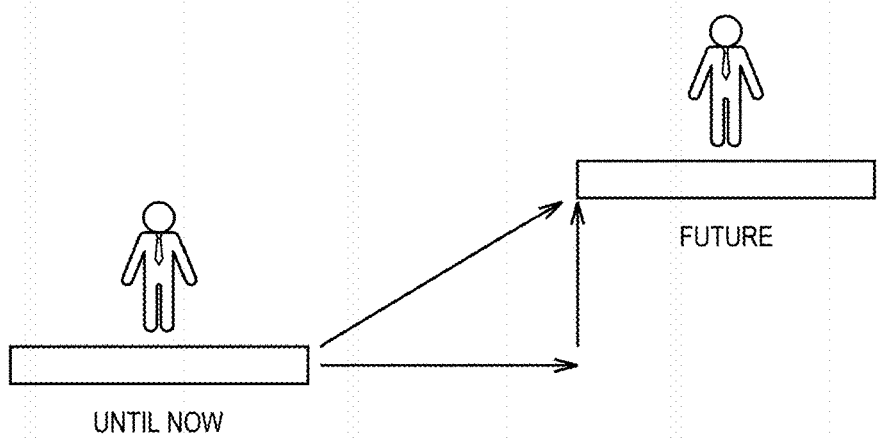
FIG. 2 is a diagram illustrating step 2 for improving a habit.

With reference to FIG. 2, in step 2, an amount of change to the value is calculated. That is, the amount of change is calculated by setting a difference between the numerical goal and the present as well as the time until the realization.

Figure 3:
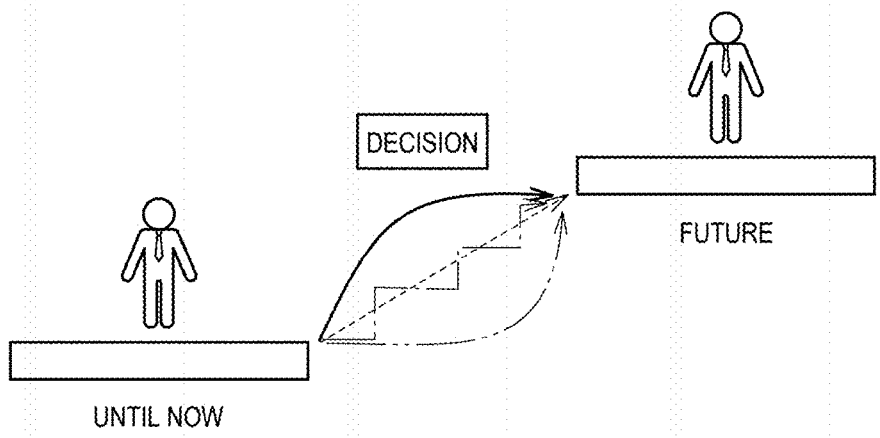
FIG. 3 is a diagram illustrating step 3 for improving a habit.

With reference to FIG. 3, in step 3, routes for realizing the change are presented. That is, a plurality of paths with the same amount of change are presented, and the route to be used is decided. The route (path) is a transition in the value of the predetermined indicator to the numerical goal of the predetermined indicator.

Figure 4:
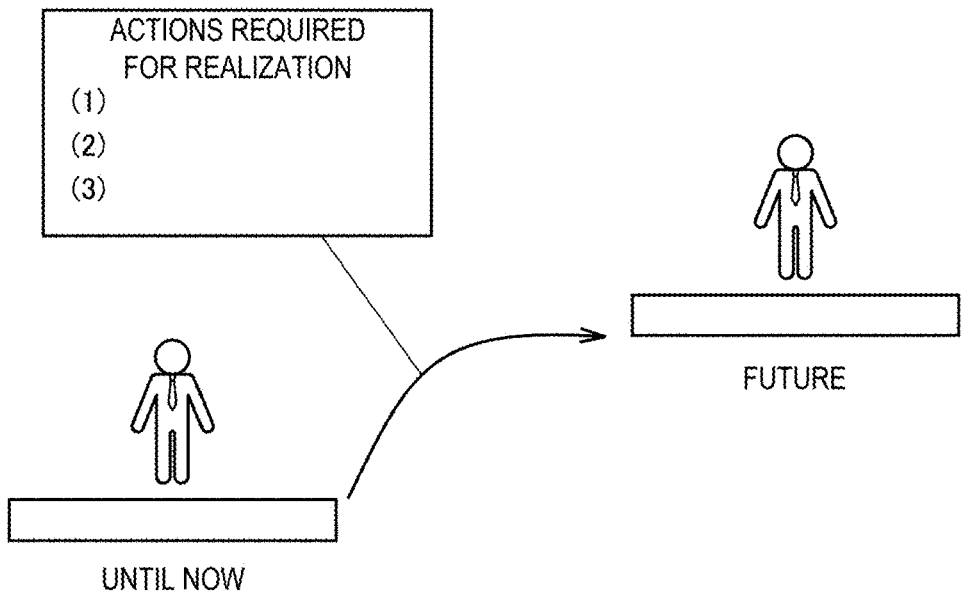
FIG. 4 is a diagram illustrating step 4 for improving a habit.

With reference to FIG. 4, in step 4, a specific action for advancing on the route is presented. That is, the specific action required to take the anticipated route is presented.

Figure 5:
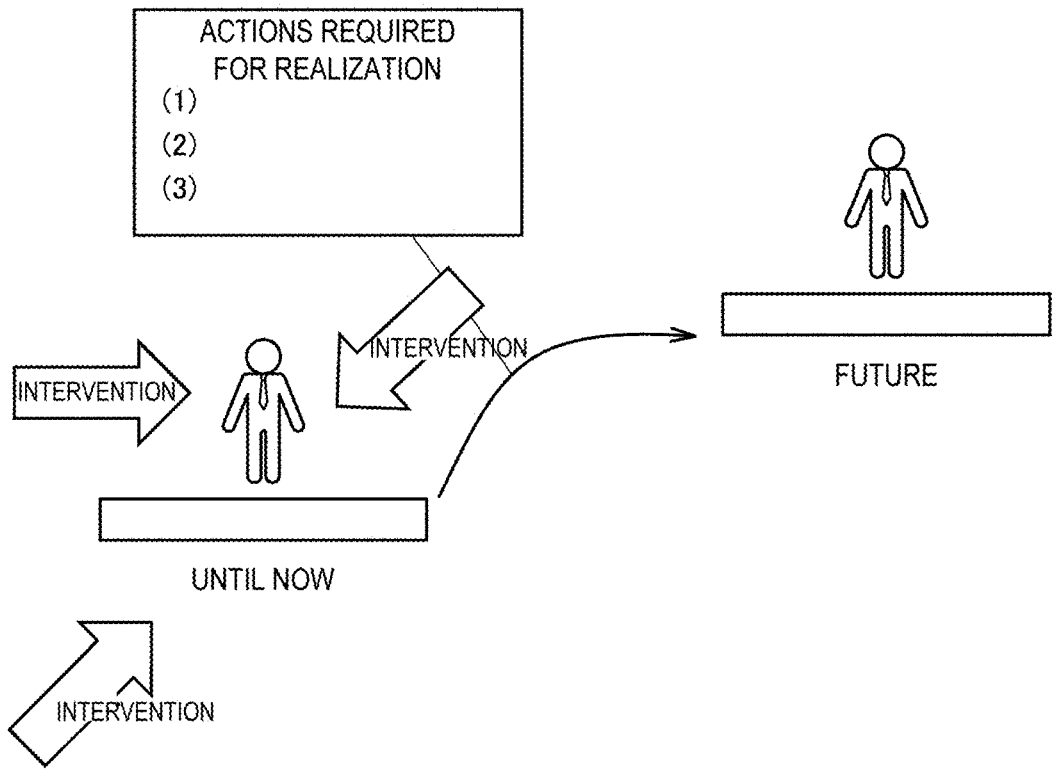
FIG. 5 is a diagram illustrating step 5 for improving a habit.

With reference to FIG. 5, in step 5, an appropriate intervention is provided using an appropriate method. That is, the appropriate content, time, location, and path of intervention are selected and provided to encourage thorough the practice of the action.

Figure 6:
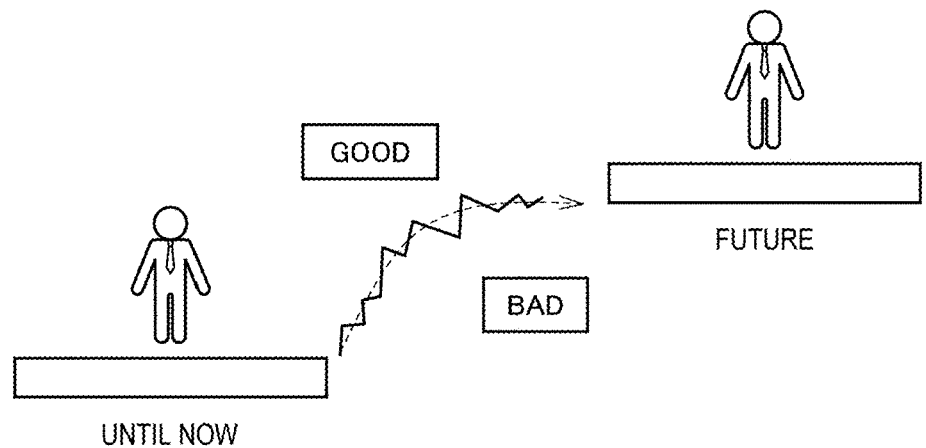
FIG. 6 is a diagram illustrating step 6 for improving a habit.

With reference to FIG. 6, in step 6, daily progress is checked and feedback is given. That is, intervention and daily progress based on the intervention are checked and evaluated against the decided route, and the intervention content, speed of change, and the like are changed according to the state of progress.

Figure 7:
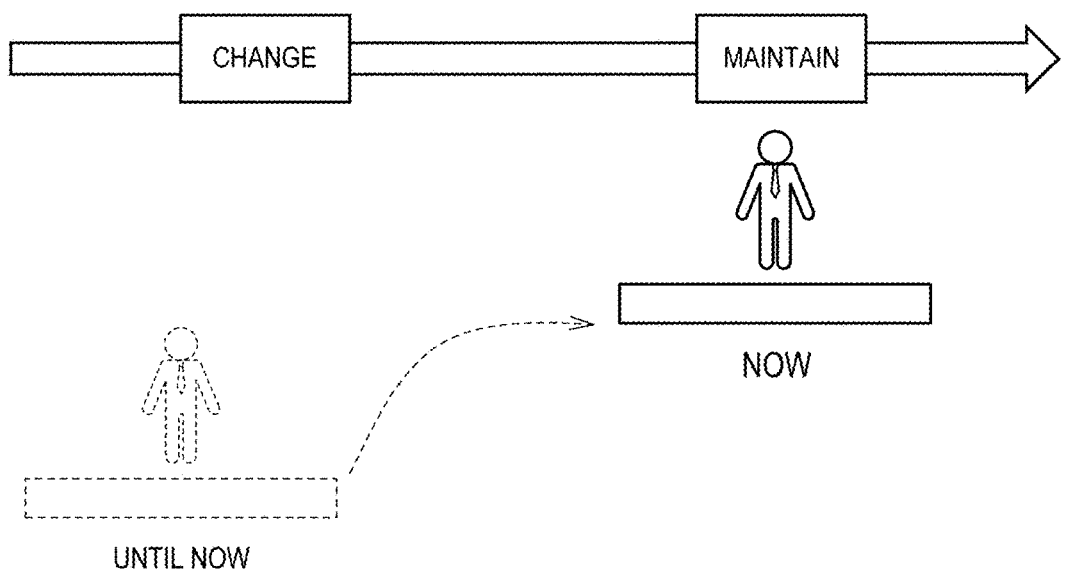
FIG. 7 is a diagram illustrating step 7 for improving a habit.

With reference to FIG. 7, in step 7, the attained stage is determined and the intervention strategy is changed. That is, as soon as the desired body shape is attained, the phase is switched and the corresponding policy is changed to "maintenance".

Figure 8:
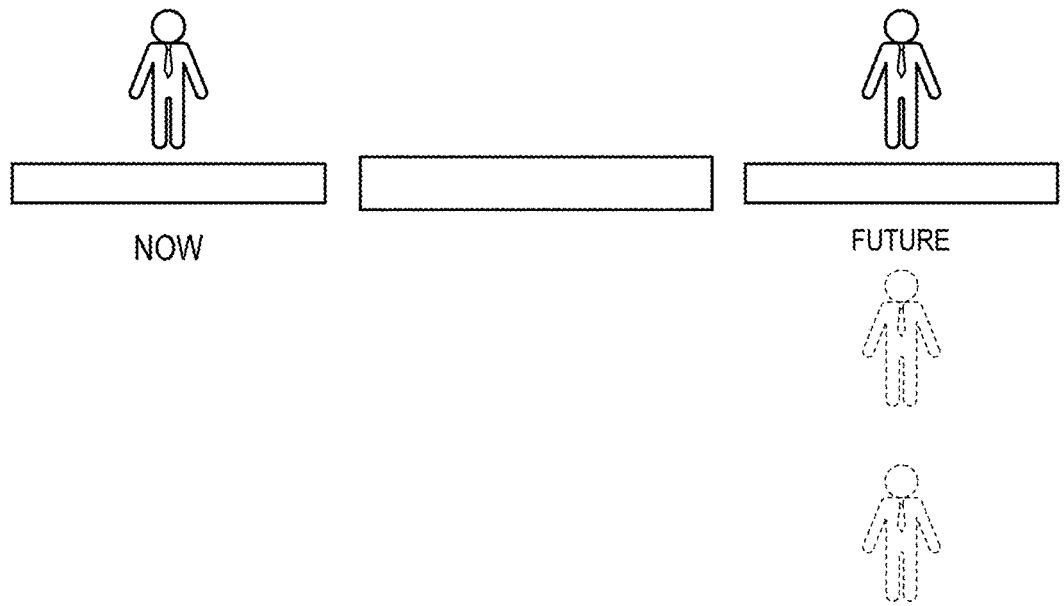
FIG. 8 is a diagram illustrating step 8 for improving a habit.

With reference to FIG. 8, in step 8, a future decline is predicted and a route is selected. That is, based on the future in which changes are anticipated according to future action states, the maintenance of the current state or gradual change is selected.

Figure 9:
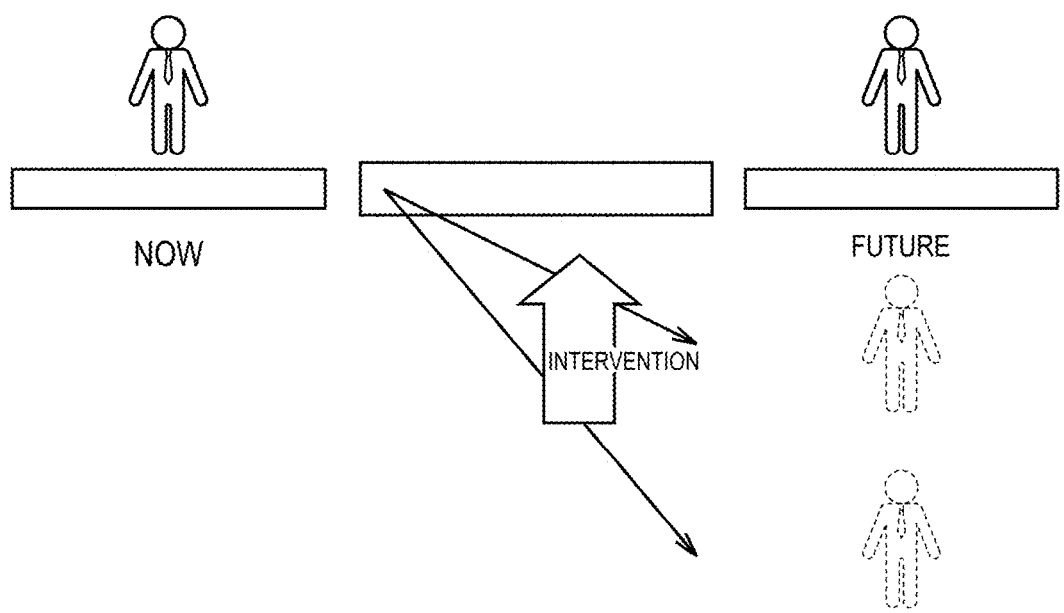
FIG. 9 is a diagram illustrating step 9 for improving a habit.

With reference to FIG. 9, in step 9, an intervention for slowing down the speed of the decline is implemented. That is, changes that may cause a deviation from the state of maintenance are proactively anticipated, and a compliment is given for intervention and a state of maintenance.

Goal Management System

Figure 10:
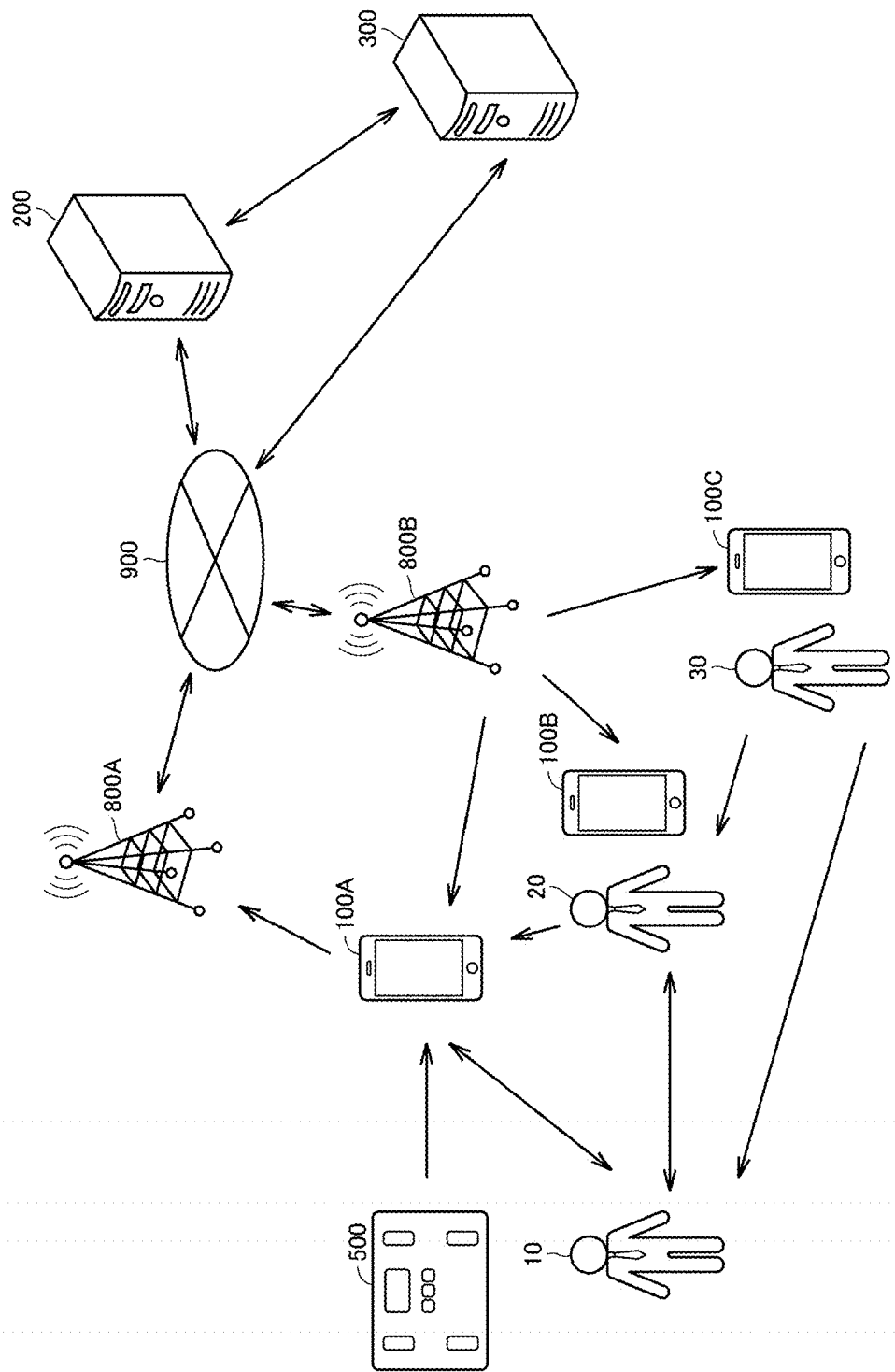
FIG. 10 is a diagram illustrating an outline of the overall configuration of a goal management system according to this embodiment.

FIG. 10 is a diagram illustrating an outline of an overall configuration of a goal management system according to this embodiment. With reference to FIG. 10, the goal management system includes: information communication terminals 100A to 100C (for example, a smartphone, a mobile phone, a personal computer (PC), a tablet PC, or the like) respectively owned by users 10, 20, 30; a server 200 for goal management; another server 300; a measuring device 500 of biological information; and communication equipment 800A, 800B of telecommunication carriers that provide communication between the information communication terminals.

The servers 200, 300 and the communication equipment 800A, 800B are communicatively connected to each other via a public network, such as the Internet and a public communication network, and a communication network 900 such as a private network such as a local area network (LAN). The information communication terminals 100A, 100B and the communication equipment 800A, 800B are communicably connected to each other by wireless communication.

Figure 11:
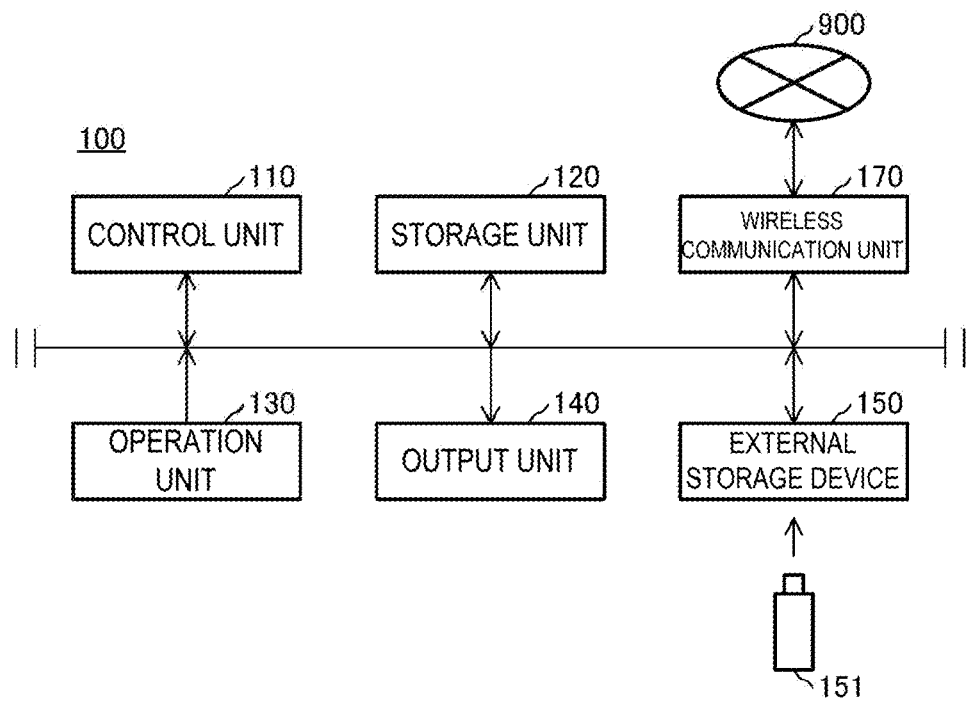
FIG. 11 is a block diagram illustrating a configuration of an information communication terminal in this embodiment.

FIG. 11 is a block diagram illustrating a configuration of the information communication terminal 100 in this embodiment. With reference to FIG. 11, the information communication terminal 100 includes: a control unit 110 for controlling the entirety of the information communication terminal 100, a storage unit 120 for storing predetermined information, an operation unit 130, an output unit 140, an external storage device 150, and a wireless communication unit 170. Note that, although not illustrated, the information communication terminal 100 also includes other components such as an audio input/output unit for inputting and outputting audio.

The control unit 110 is composed of a central processing unit (CPU) and an auxiliary circuit thereof, controls the storage unit 120, the operation unit 130, the output unit 140, and the wireless communication unit 170, executes a predetermined process in accordance with a program or data stored in the storage unit 120, processes data input from the operation unit 130 and the wireless communication unit 170, stores the processed data in the storage unit 120, and outputs the processed data to the output unit 140 and the wireless communication unit 170.

The storage unit 120 includes: a random access memory (RAM), which is used as a work area required to execute a program by the control unit 110, and a read only memory (ROM) for storing a program for execution by the control unit 110. Further, the RAM stores programs and data for executing a predetermined process read from the operation unit 130, the wireless communication unit 160, or the external storage device 150. Furthermore, a hard disk drive or a memory card may be used as an auxiliary storage device for supplementing the storage area of the RAM.

The external storage device 150 is composed of a memory card reader/writer. The external storage device 150 electrically records predetermined data or a program received from the control unit 110 in a recording medium 151 such as a memory card or a universal serial bus (USB) memory and reads and relays the predetermined data or the program from the recording medium 151 to the control unit 110. Note that the external storage device 150 may be composed of a storage device such as a hard disk drive, a flexible disk drive, a magneto-optical disk (MO) drive, a compact disc (CD) drive, or a digital versatile disk (DVD) drive.

The operation unit 130 includes a touch panel and operation buttons for inputting numbers, alphabetical characters, other characters, and the like, for phone numbers, various data, and the like. Note that the operation unit 130 may include a portion for other operations. The operation unit 130 is operated by a user, thereby transmitting an operation signal corresponding to the operation from the operation unit 130 to the control unit 110. The control unit 110 controls each unit of the information communication terminal 100 in accordance with the operation signal from the operation unit 130.

The wireless communication unit 170 is controlled by the control unit 110 to receive a wireless signal from another information communication terminal 100 or a fixed phone of a communication partner via the communication equipment 800 of the telecommunication carrier and an antenna, to convert the received wireless signal into an audio signal, and to transmit the converted audio signal to the audio input/output unit, also, to convert the audio signal from the audio input/output unit into a wireless signal and to transmit the wireless signal to another information communication terminal 100 or a fixed phone of the communication partner via an antenna and the communication equipment 800 of the telecommunication carrier.

Further, the wireless communication unit 170 is controlled by the control unit 110 to receive a wireless signal via a device capable of data communication, such as a server or another information communication terminal 100, for example, via the communication equipment 800 of the telecommunication carrier and an antenna, to convert the received wireless signal into data, to store the converted data in the storage unit 120, and to transmit the converted data to the output unit 140 to display the data, also, to convert the data to be transmitted into a wireless signal and to transmit the wireless signal to a server of the data communication destination or another information communication terminal 100 via an antenna and the communication equipment 800 of the telecommunication carrier.

Further, the wireless communication unit 170 is controlled by the control unit 110 to exchange data with other devices capable of network communication, such as a server or another information communication terminal 100, for example, via a public wireless LAN or a private network wireless LAN.

The output unit 140 includes a display and a speaker. The output unit 140 is controlled by the control unit 110 to display video signals and output audio signals obtained by converting, by the control unit 110, information received by the wireless communication unit 170, information stored in the storage unit 120, or information read from the recording medium 151 by the external storage device 150 as video on a display and as audio from a speaker, respectively.

Figure 12:
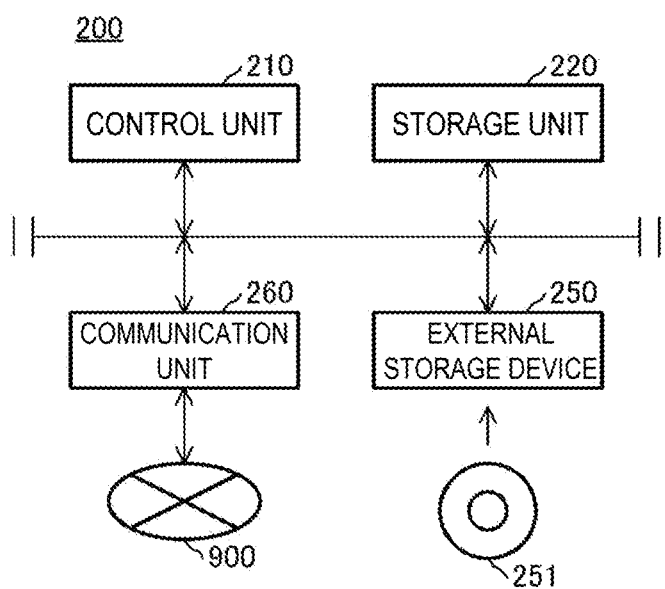
FIG. 12 is a block diagram illustrating a configuration of a server for goal management in this embodiment.

FIG. 12 is a block diagram illustrating a configuration of the server 200 for goal management in this embodiment. With reference to FIG. 12, the server 200 includes: a control unit 210 for controlling the entirety of the server 200, a storage unit 220 for storing predetermined information, an external storage device 250 for supplementing the storage unit 220 and storing predetermined information, and a communication unit 260 for communicating with an external device via the communication network 900.

The storage unit 220 is similar to the storage unit 120 of the information communication terminal 100 described in FIG. 11, and thus redundant descriptions thereof will not be repeated.

The communication unit 260 transmits and receives data to and from an external device via the communication network 900 using a predetermined protocol. The communication unit 260 transmits data received from the control unit 210 to the outside and relays data received from the outside to the control unit 210.

The external storage device 250 is composed of a storage device such as a hard disk drive, a flexible disk drive, an MO drive, a CD drive, a DVD drive, or a memory card reader/writer. The external storage device 250 electromagnetically, optically, or electrically records predetermined data or a program received from the control unit 210 in a recording medium 251 or reads and relays predetermined data or a program from the recording medium 251 to the control unit 210.

Examples of the recording medium 251 include a magnetic disk such as a hard disk or a flexible disk; an optical disk such as a compact disk read only memory (CD-ROM), a compact disk recordable (CD-R), a compact disk rewritable (CD-RW), a digital versatile disk read only memory (DVD-ROM), a digital versatile disk recordable (DVD-R), a digital versatile disk rerecordable disc (DVD-RW), a digital versatile disk random access memory (DVD-RAM), a DVD+R, a digital versatile disk rewritable (DVD+RW), a Blu-ray (trade name) disc recordable (BD-R), a Blu-ray (trade name) disc rewritable (BD-RE), and a Blu-ray (trade name) disc read only memory (BD ROM); a magneto-optical disk such as an MO; a memory card; a USB memory; or the like.

The control unit 210 has a configuration similar to that of the control unit 110 of the information communication terminal 100 described using FIG. 11. The control unit 210 controls the storage unit 220, the external storage device 250, and the communication unit 260, executes a predetermined process in accordance with the programs and data stored in the storage unit 220, processes data input from the external storage device 250 or the communication unit 260, stores the processed data in the storage unit 220 or the recording medium 251 of the external storage device 250, and outputs the processed data from the communication unit 260.

Note that, in this embodiment, while the server 200 does not include an operation unit or a display unit but is operated by an operation from an operation unit of an external device and outputs information to the display unit of the external device, the server is not limited thereto and may include a configuration of an operation unit and a display unit. The operation unit may include a keyboard and a mouse, and an operation signal, indicating the operation content input to the server 200 by the operation of the keyboard and the mouse of the operation unit, may be relayed to the control unit 210. The display unit may include a display, and the display may display an image corresponding to image data received from control unit 210.

Note that the configuration of the other server 300 is the same as the configuration of the server 200, and thus redundant description thereof will not be repeated.

Figure 13:
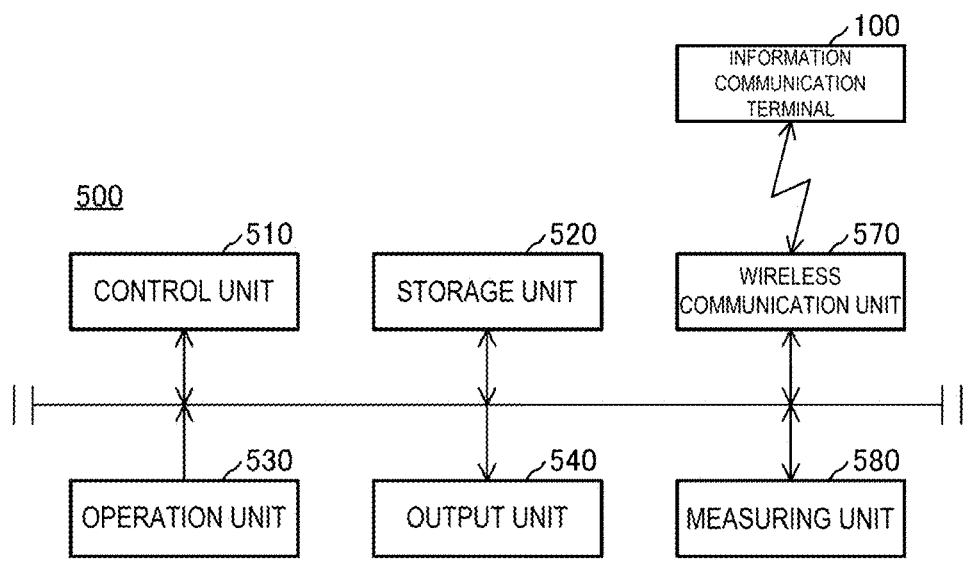
FIG. 13 is a block diagram illustrating a configuration of a measuring device for biological information in this embodiment.

FIG. 13 is a block diagram illustrating a configuration of the measuring device 500 for biological information in this embodiment. With reference to FIG. 13, the measuring device 500 for biological information, such as a body composition meter as illustrated in FIG. 13, includes: a control unit 510 for controlling an entirety of the measuring device 500, a storage unit 520 for storing predetermined information, an operation unit 530, an output unit 540, a wireless communication unit 570, and a measuring unit 580.

The control unit 510, the storage unit 520, the operation unit 530, the output unit 540, and the wireless communication unit 570 are the same as the control unit 110, the storage unit 120, the operation unit 130, the output unit 140, and the wireless communication unit 170 of the information communication terminal 100 described in FIG. 11, respectively, and thus redundant descriptions thereof will not be repeated. Note that the wireless communication unit 570 may be capable of communicating with the information communication terminal 100 directly or via the communication network 900, the communication equipment 800 of a telecommunication carrier, or the like.

The measuring unit 580 is controlled by the control unit 110 to measure predetermined biological information of the plurality of sets of biological information of the user, and transmit measurement result information to the control unit 110. The biological information includes: information indicating the state of the body and information indicating physical activity and movement and specifically includes various indicators related to the body, such as weight, chest measurement, waist measurement, height, body composition values (body fat percentage, visceral fat level, subcutaneous fat percentage, basal metabolism, skeletal muscle ratio, muscle mass percentage, body mass index (BMI), body age, and the like), activity level, step count, blood pressure value, heartbeat (pulse rate), body temperature, respiration rate, indicator values related to blood (blood glucose value, neutral fat level, cholesterol level, and the like), calorie consumption, food intake, moisture intake, excretion amount, perspiration amount, lung capacity, and amount of sleep.

Figure 14:
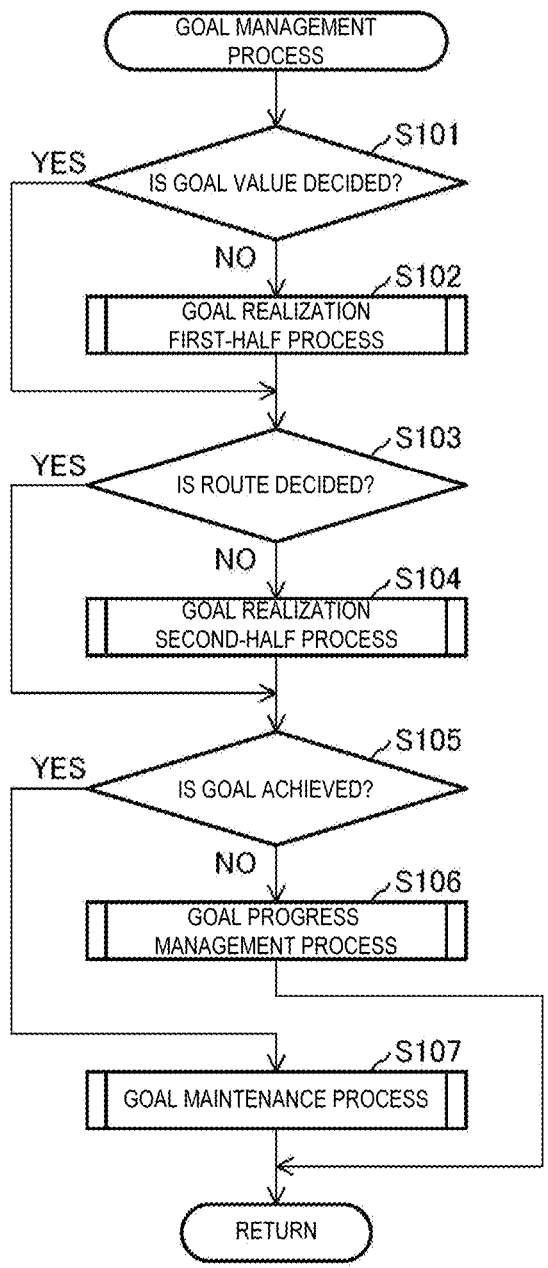
FIG. 14 is a flowchart illustrating a flow of a goal management process executed by the server for goal management in this embodiment.

FIG. 14 is a flowchart illustrating a flow of a goal management process executed by the server 200 for goal management in this embodiment. With reference to FIG. 14, the control unit 210 of the server 200 determines whether a goal value for improvement in the biological information has already been decided (step S101). When it is determined that a goal value has not been decided (NO in step S101), the control unit 210 executes a goal realization first-half process illustrated in FIG. 15 described later (step S102).

When the goal value has been decided (YES in step S101) and after step S102, the control unit 210 determines whether the route to goal attainment has already been decided (step S103). When it is determined that the route has not been decided (NO in step S103), the control unit 210 executes a goal realization second-half process illustrated in FIG. 29 described later (step S104).

When it is determined that the route has been decided (YES in step S103) and after step S104, the control unit 210 determines whether the decided goal has been attained (step S105). When it is determined that the goal has not been attained (NO in step S105), the control unit 210 executes a goal progress management process (step S106).

When it is determined that the goal has been attained (YES in step S105), the control unit 210 executes a goal maintenance process (step S107).

Goal Realization First-Half Process

Figures 15, 16:
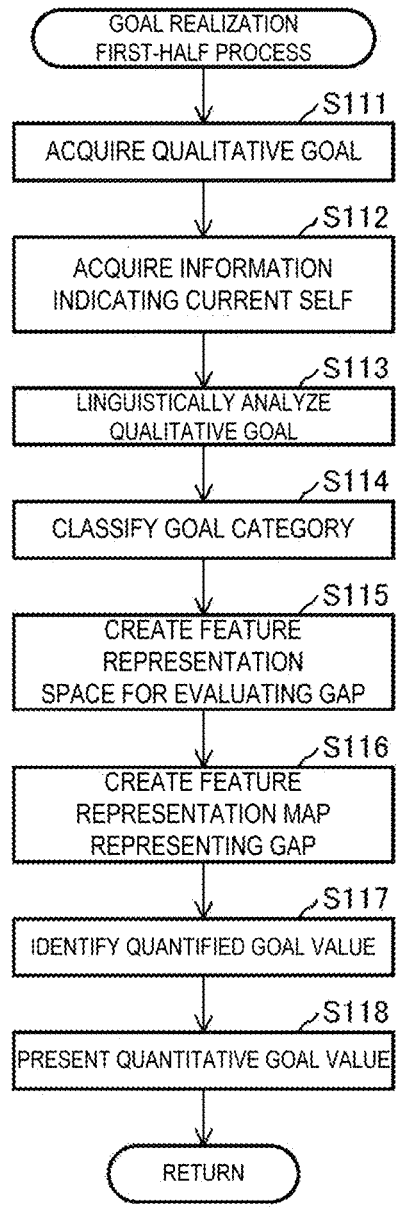
FIG. 15 is a flowchart illustrating a flow of a goal realization first-half process executed by the server for goal management in this embodiment.
FIG. 16 is a diagram illustrating an example of morphological analysis in this embodiment.

FIG. 15 is a flowchart illustrating a flow of the goal realization first-half process executed by the server 200 for goal management in this embodiment. With reference to FIG. 15, the control unit 210 of the server 200 acquires a qualitative goal (step S111).

Specifically, the control unit 210 acquires a qualitative goal input using the information communication terminal 100A by the user 10 and stores the acquired information in the storage unit 220 for each user. The method of inputting the information in the information communication terminal 100A may be any method and, for example, may be manual input or voice input or may be input by an interactive method using manual input or voice input.

Further, the control unit 210 acquires information indicating the current self (step S112). Specifically, the control unit 210 acquires attributes (age, gender, family structure, and the like) of the user input by the user 10 using the information communication terminal 100A and stores the acquired information in the storage unit 220 for each user.

Next, the control unit 210 linguistically analyzes the qualitative goal acquired in step S111 (step S113). Specifically, the qualitative goal of the user 10 entered as characters is given meaning by morphological analysis or the like. For the morphological analysis, known techniques can be used.

FIG. 16 is a diagram illustrating an example of the morphological analysis in this embodiment. With reference to FIG. 16, in the morphological analysis, the language is divided into units having meanings. For example, when the user 10 enters "Ideal dad" as a qualitative goal, the language is divided into "ideal" and "dad".

Returning to FIG. 15, the control unit 210 classifies the goal into a category (step S114). Specifically, the goal is classified into a category (body composition, blood pressure, sleep, or the like) from the attributes of the meaning of the goal based on the language information analyzed in step S113.

Figure 17:
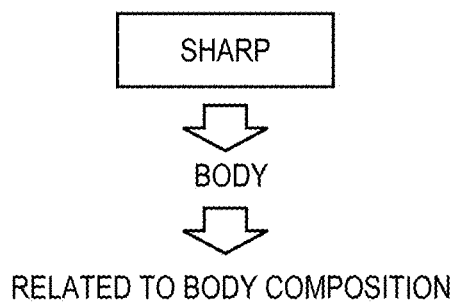
FIG. 17 is a diagram illustrating an example of classification of the goal into a category in this embodiment.

FIG. 17 is a diagram illustrating an example of classification of the goal into a category in this embodiment. With reference to FIG. 17, among the morphemes divided in step S113, "ideal" is language related to "body type" and thus is classified into a category related to body composition.

Returning to FIG. 15, the control unit 210 creates a feature representation space for gap evaluation (step S115). Specifically, on the basis of the classified category in step S114, a feature amount for evaluating the gap from the goal is extracted, and this feature amount constitutes an axis of a multidimensional space. This multidimensional space is referred to as a feature representation space.

Figure 18:
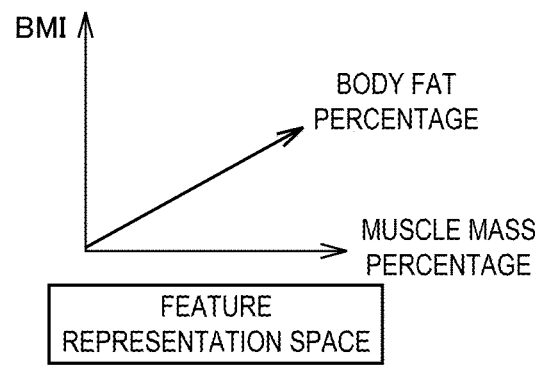
FIG. 18 is a diagram illustrating an example of a feature representation space in this embodiment.

FIG. 18 is a diagram illustrating an example of the feature representation space in this embodiment. With reference to FIG. 18, for example, when "BMI", "percent body fat percentage", and "muscle mass percentage" are stored in the storage unit 220 of the server 200 for goal management as indicators related to the category for body composition, a feature representation space including a "BMI" axis, a "body fat percentage" axis, and a "muscle mass percentage" axis is created.

Returning to FIG. 15, the control unit 210 creates the feature representation map representing the gap (step S116). Specifically, from the information of the attributes of the user 10 acquired in step S112 and the meanings of the morphemes divided in step S113, a range on the feature representation space created in step S114 is created as a feature representation map.

Figure 19:
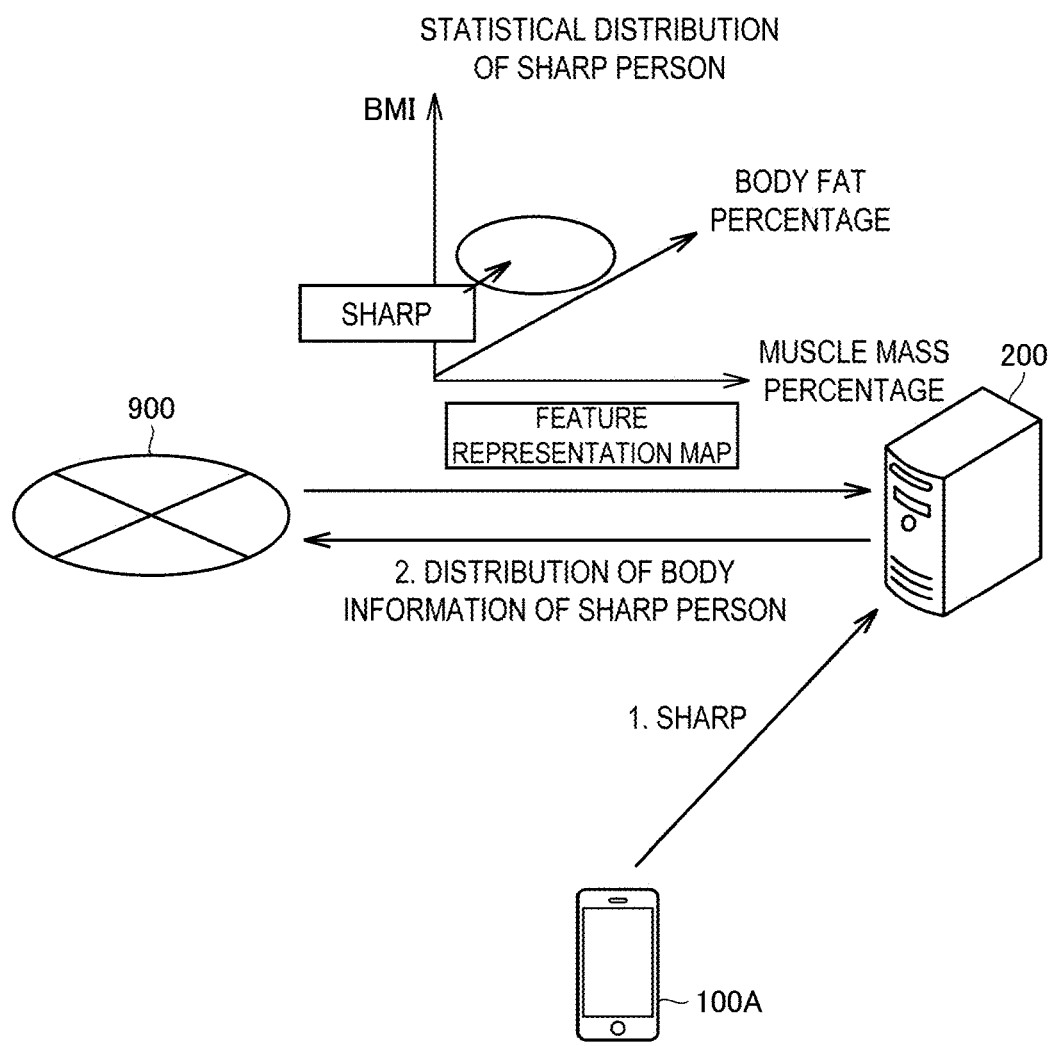
FIG. 19 is a first diagram illustrating an example of a creation process for a feature representation map in this embodiment.

FIG. 19 is a first diagram illustrating an example of a creation process for the feature representation map in this embodiment. With reference to FIG. 19, the server 200 acquires statistical information of an "ideal" person from the other server 300 or another information communication terminal 100 via the communication network 900 in advance and stores the statistical information of an "ideal" person in the storage unit 220 as a database of values of indicators for an "ideal" person. The control unit 210 creates a distribution of an "ideal" person in the feature representation space on the basis of the statistical information of an "ideal" person stored in this storage unit 220.

Figures 20, 21:
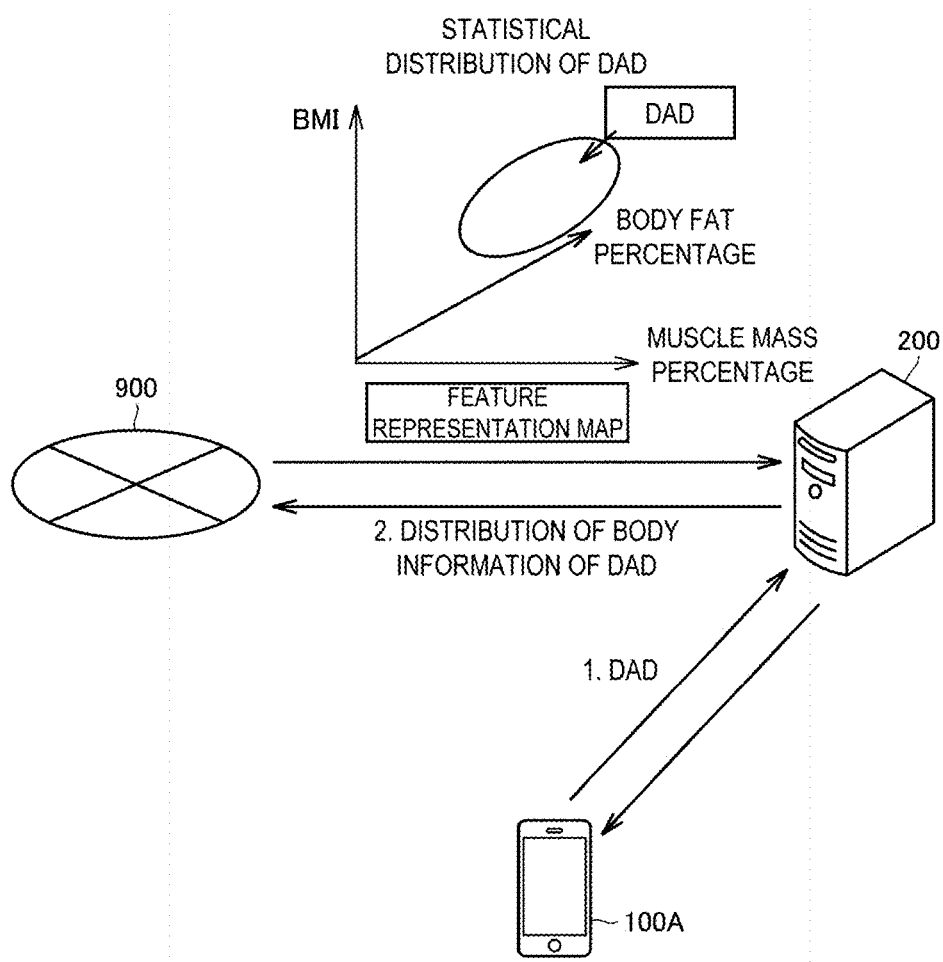
FIG. 20 is a second diagram illustrating an example of the creation process for the feature representation map in this embodiment.
FIG. 21 shows an example of a database at an initial stage of values of indicators related to a body composition of an "ideal" person in this embodiment.

FIG. 20 is a second diagram illustrating an example of a creation process for the feature representation map in this embodiment. With reference to FIG. 20, the server 200 acquires statistical information of a "dad" from the other server 300 or another information communication terminal 100 via the communication network 900 in advance and stores the statistical information of a "dad" in the storage unit 220 as a database of values of indicators for a "dad". The control unit 210 creates a distribution of a "dad" in the feature representation space on the basis of the statistical information of a "dad" stored in this storage unit 220.

FIG. 21 shows an example of a database at an initial stage of the values of indicators related to body composition of an "ideal" person in this embodiment. With reference to FIG. 21, at an initial stage of database creation, the server 200 stores the values of indicators corresponding to basic classification items (here, the item "age") as a database since there is little data.

FIG. 22 shows an example of a database after data accumulation of the values of indicators related to body composition of an "ideal" person in this embodiment. With reference to FIG. 22, as data accumulates and increases, the server 200 can store values of indicators corresponding to other classification items (here, the items classification (1), classification (2)) as a database. Further, new indicators (here, chest measurement, waist measurement) can also be included.

Figure 23:
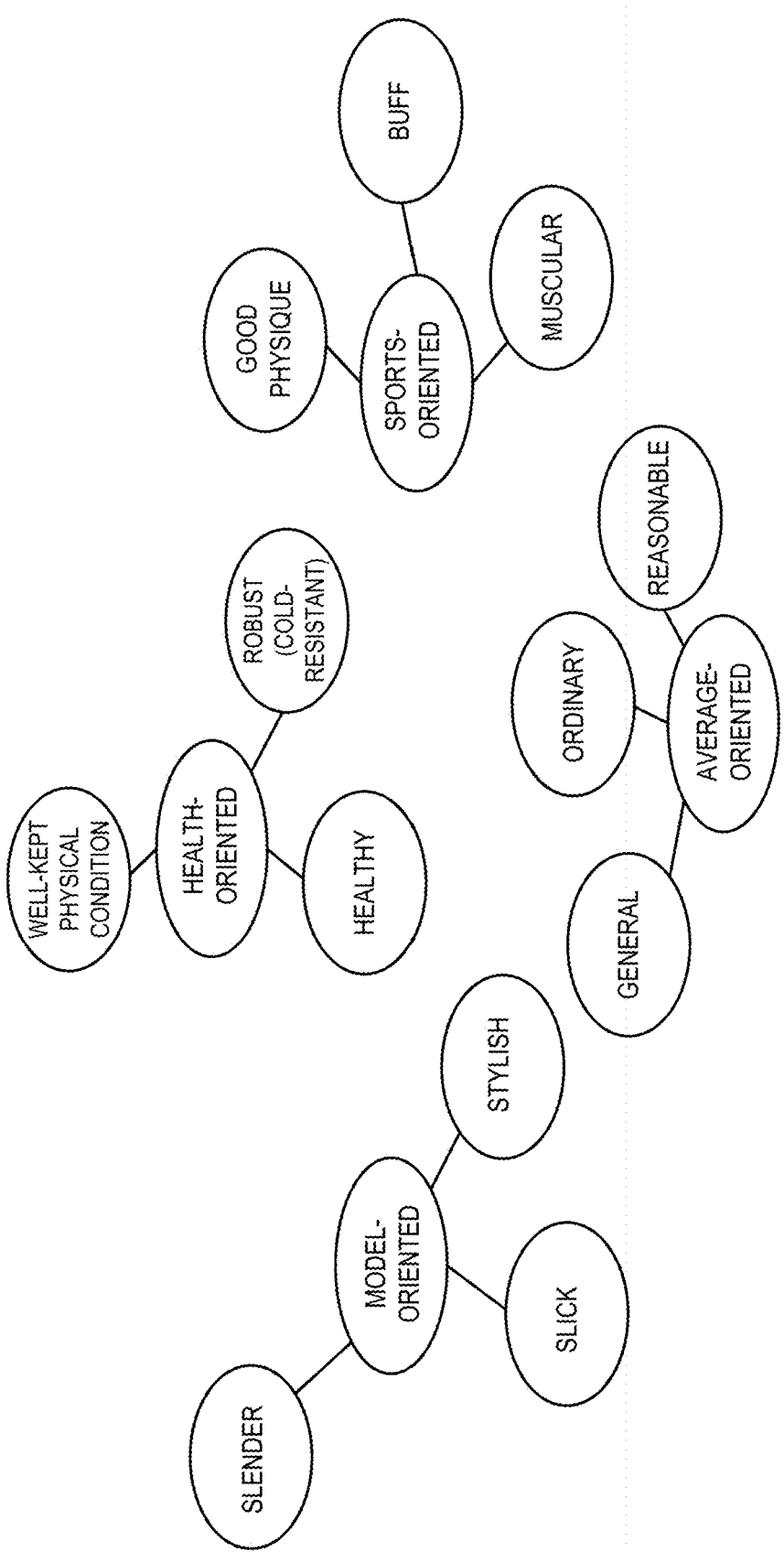
FIG. 23 is a diagram illustrating an example of a language database for categories related to a body composition in this embodiment.

FIG. 23 is a diagram illustrating an example of a language database for categories related to body composition in this embodiment. With reference to FIG. 23, when the data of the database of the indicators is not sufficient, abstracted classification items (model-oriented, sports-oriented, health-oriented, average-oriented) are used, as indicated by classification (1) in FIG. 22. For abstraction, a language database such as a thesaurus or the like illustrated in FIG. 23 that is obtained by focusing on the meaning of language is used.

As the data of the database of indicators increases, more specific classification items (thin, slim, slender, well-built, thick, muscular, health-conscious, robust (cold-resistant), healthy, ordinary, average, reasonable) as indicated by classification (2) in FIG. 22. The values of the indicators for each classification item are collected with reference to the values of persons who had the classification item or similar language as a goal and achieved the goal.

Returning to FIG. 15, the control unit 210 identifies the quantified goal value (step S117). Specifically, a range of each feature amount indicating a range of an overlapping portion of the ranges on the feature representation map created in step S116 is identified as a quantitative goal value and stored in the storage unit 220.

Figure 24:
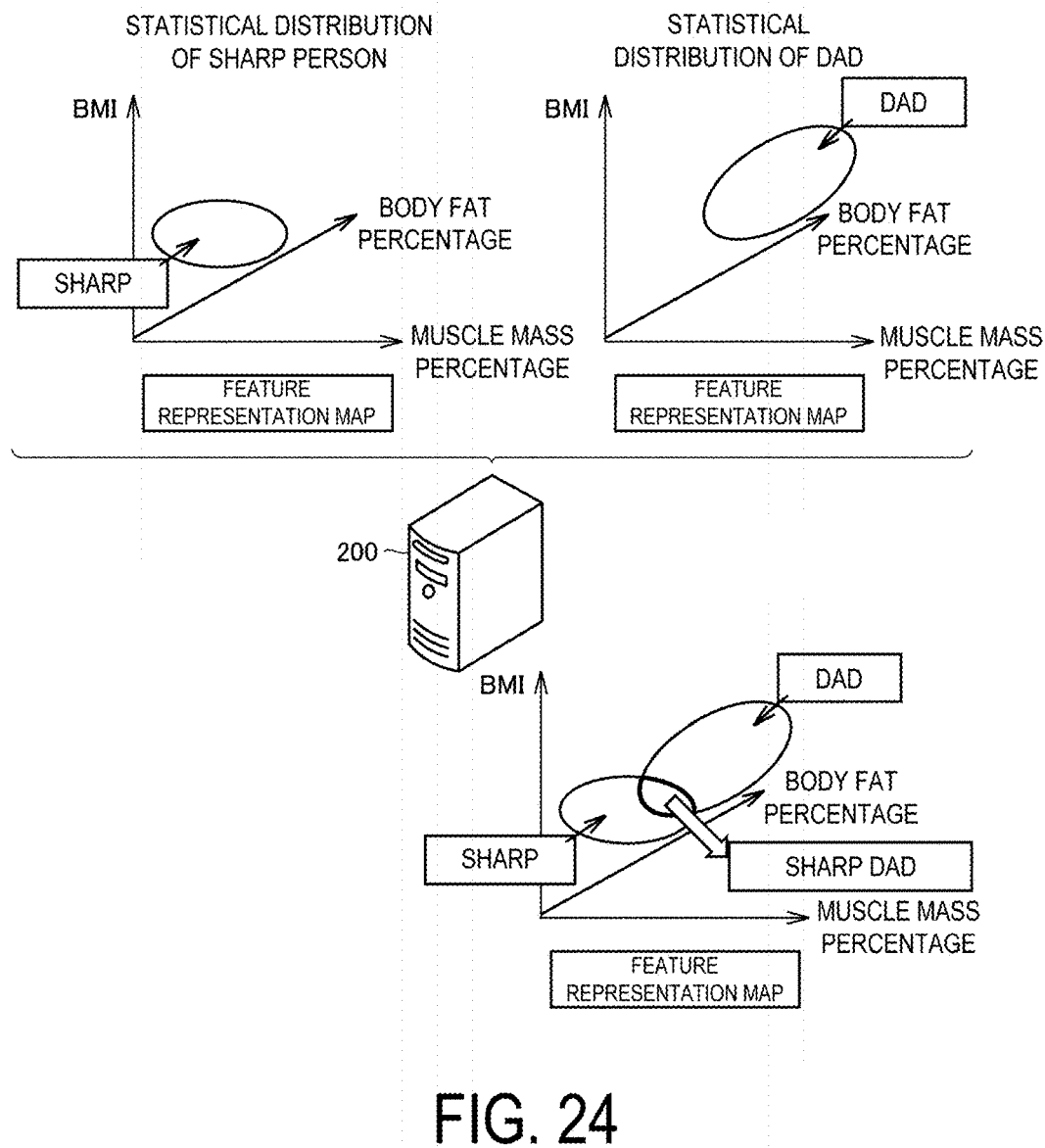
FIG. 24 is a first diagram illustrating an example of an identification process for a quantitative goal value from a feature representation map in this embodiment.

FIG. 24 is a first diagram illustrating an example of an identification process for the quantitative goal value from the feature representation map in this embodiment. With reference to FIG. 24, when the feature representation map of an "ideal" person illustrated in FIG. 19 and the feature representation map of a "dad" illustrated in FIG. 20 are combined, a feature representation map of a "ideal dad" is obtained.

Figure 25:
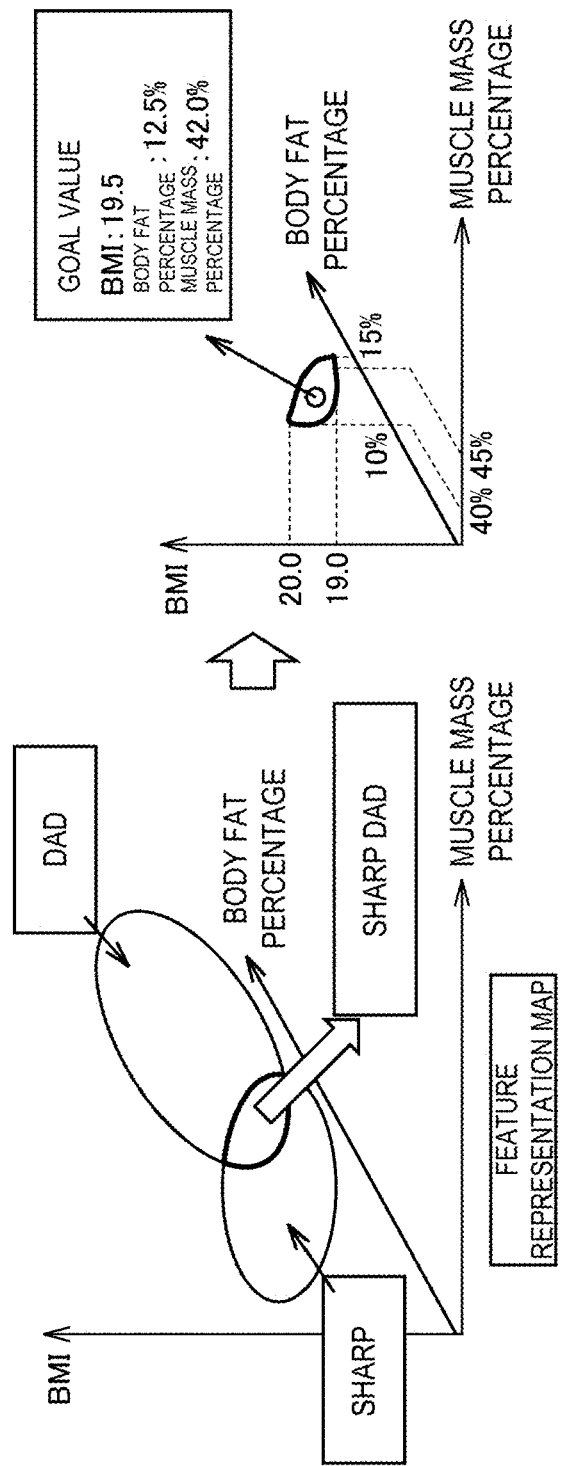
FIG. 25 is a second diagram illustrating an example of the identification process for the quantitative goal value from the feature representation map in this embodiment.

FIG. 25 is a second diagram illustrating an example of an identification process for the quantitative goal value from the feature representation map in this embodiment. With reference to FIG. 25, a value of a point (here, a center point of gravity) within a range of an overlapping portion of ranges of a plurality (here, two) of feature representation maps is referred to as a quantitative goal value.

While a center point of gravity is used herein, another point may be used as long as the point is within the overlapping portion, and this point may be obtained by combining median values of the range of each axis in the range of the overlapping portion (in FIG. 25, the BMI is from 19.0 to 20.0, the body fat percentage is from 10 to 15, and the muscle mass percentage is from 40 to 45, and thus the respective median values of the goal value of the BMI, the body fat percentage, and muscle mass percentage are 19.5, 12.5, 42.5).

Figure 26:
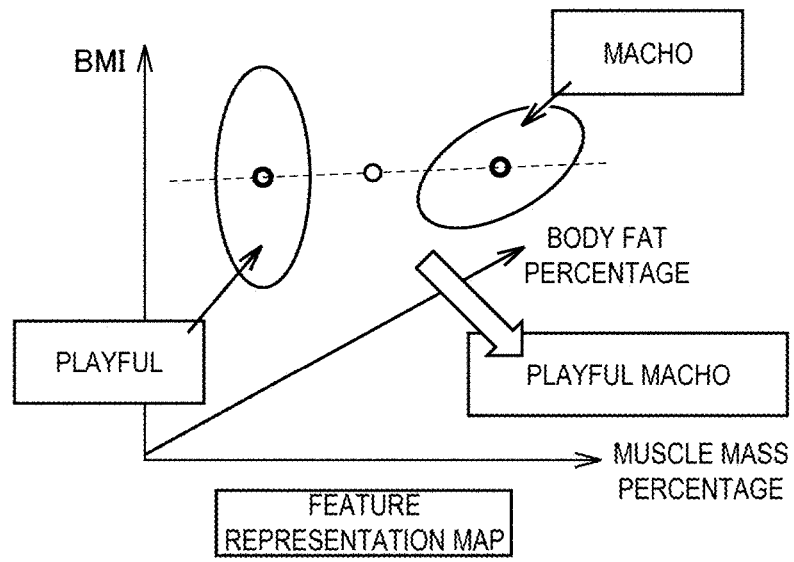
FIG. 26 is a third diagram illustrating an example of the identification process for the quantitative goal value from the feature representation map in this embodiment.

FIG. 26 is a third diagram illustrating an example of an identification process for the quantitative goal value from the feature representation map in this embodiment. With reference to FIG. 26, when the ranges of the plurality of feature representation maps do not overlap, the value of the point between each range (for example, the center point of the center points of gravity of each range) is a quantitative goal value.

With reference to FIG. 15, the control unit 210 transmits the quantitative goal value identified in step S117 to the information communication terminal 100A of the user 10 for presentation on the information communication terminal 100A (step S118). Subsequently, the control unit 210 returns the process to be executed to the process of the calling source.

Figure 27:
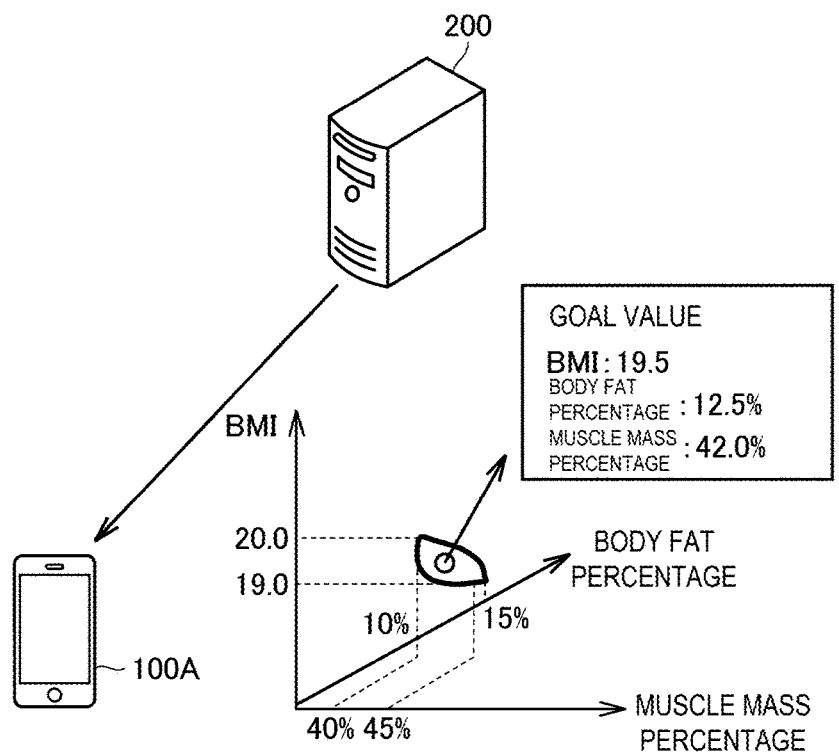
FIG. 27 is a diagram for explaining the presentation of the quantitative goal value in this embodiment.

FIG. 27 is a diagram for explaining the presentation of a quantitative goal value in this embodiment. With reference to FIG. 27, a quantitative goal value is transmitted from the server 200 configured to manage goals the information communication terminal 100A of the user 10.

Figure 28:
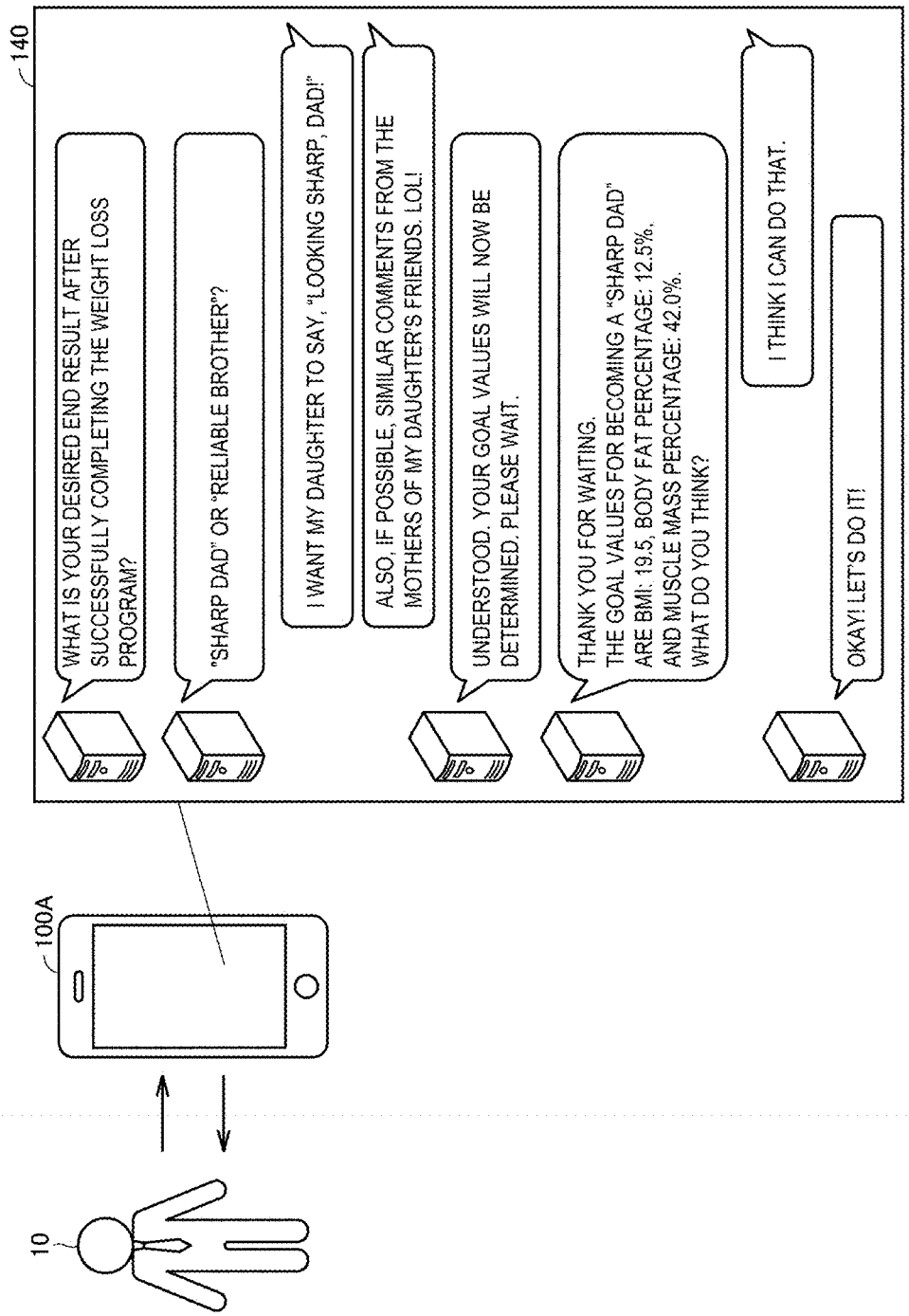
FIG. 28 is a diagram illustrating an example of a display screen displayed on a display unit of the information communication terminal in the goal realization first-half process in this embodiment.

FIG. 28 is a diagram illustrating an example of a display screen displayed on the output unit 140 of the information communication terminal 100A in the goal realization first-half process in this embodiment. With reference to FIG. 28, the five speech balloons from the top are displayed in step S111 of the goal realization first-half process illustrated in FIG. 15. Note that the exchange in step S112 is not illustrated in FIG. 28. The sixth to eighth speech balloons from the top are displayed in step S118 of FIG. 15.

Goal Realization Second-Half Process

Figure 29:
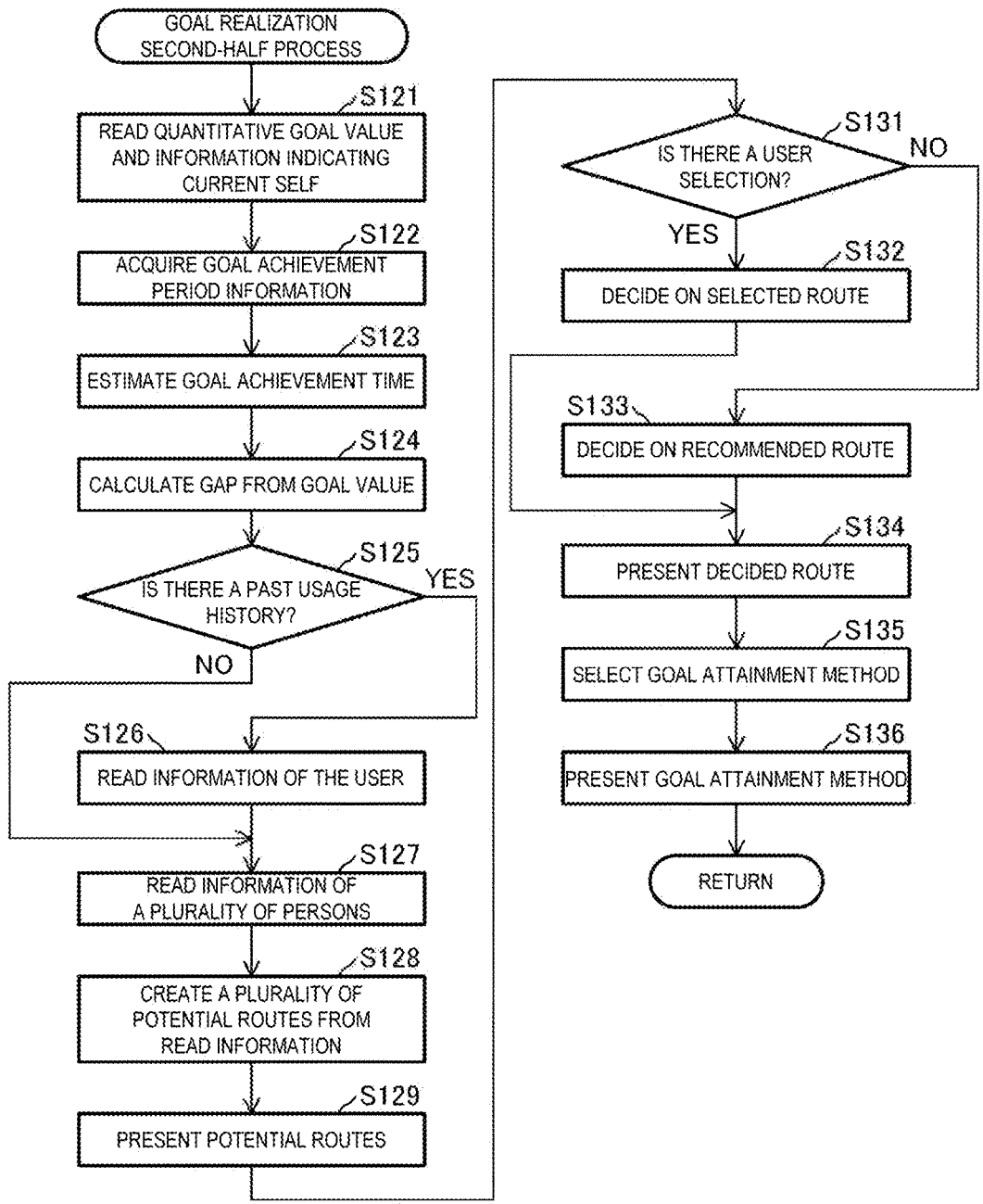
FIG. 29 is a flowchart illustrating a flow of a goal realization second-half process executed by the server for goal management in this embodiment.

FIG. 29 is a flowchart illustrating a flow of the goal realization second-half process executed by the server 200 for goal management in this embodiment. With reference to FIG. 29, the control unit 210 of the server 200 reads the quantitative goal value and information indicating the current self stored in the storage unit 220 in the process of FIG. 15 (step S121).

Next, the control unit 210 acquires information related to the period for goal attainment (step S122) and estimates the goal attainment time (step S123).

Figure 30:
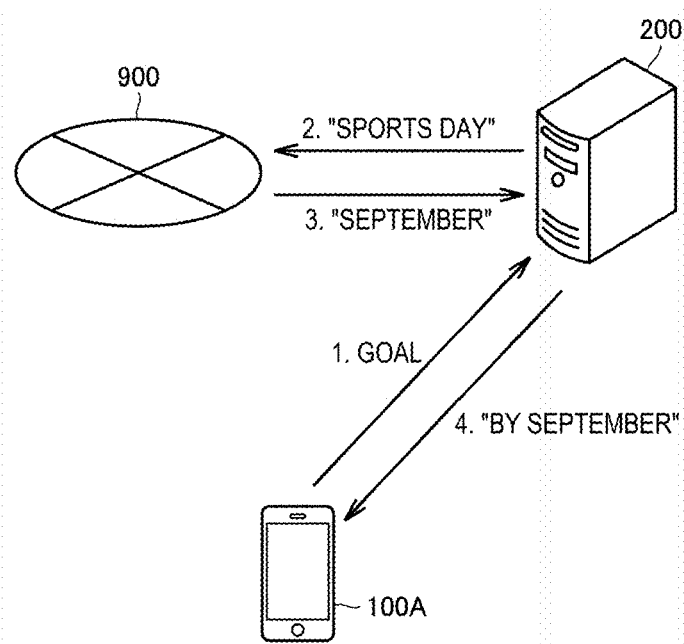
FIG. 30 is a diagram illustrating an example of a process of acquiring information related to a period for goal attainment in this embodiment.

FIG. 30 is a diagram illustrating an example of a process of acquiring information related to the period of goal attainment in this embodiment. With reference to FIG. 30, when, for example, the user 10 inputs, as a goal, the information "I want to look ideal for my daughter on a sport day" using the information communication terminal 100A, the control unit 210 of the server 200 identifies that the "sport day" of the daughter is in "September" on the basis of information from the other server 300 and the like connected to the communication network 900. As a result, the deadline for goal attainment is set to "by September".

Further, when the user 10 inputs, as a goal, "I want to fit nicely into a T-shirt in July", the control unit 210 sets the goal attainment period as July.

Figure 31:
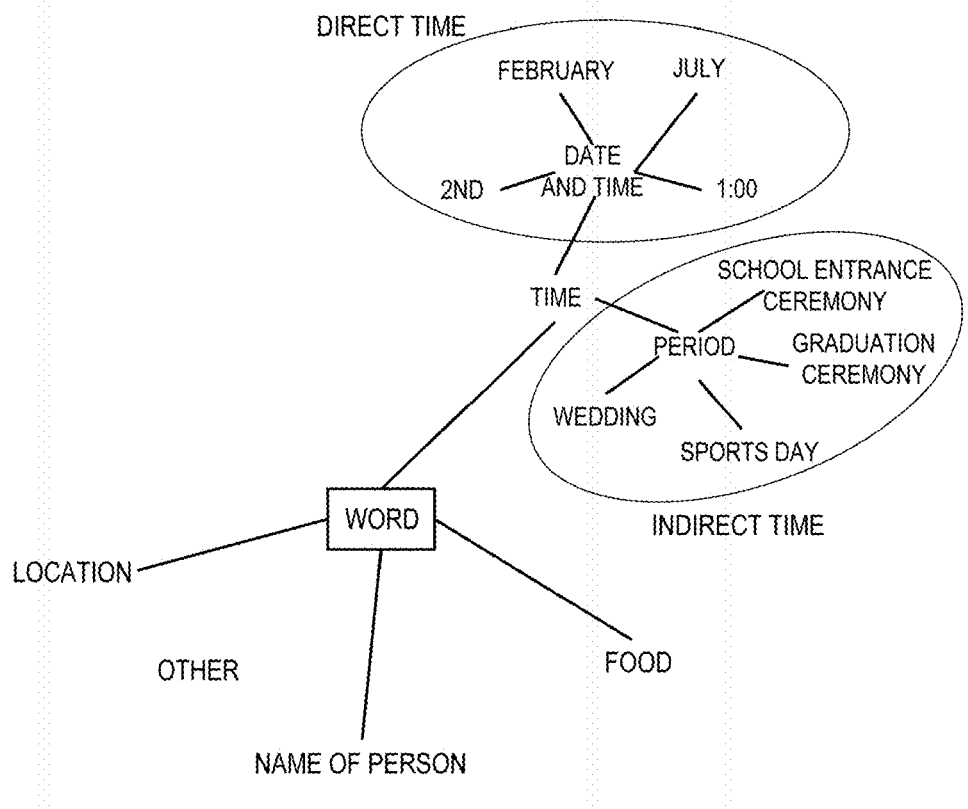
FIG. 31 is a diagram illustrating an example of a meaning analysis of words specifying a time in this embodiment.

FIG. 31 is a diagram illustrating an example of a meaning analysis of words specifying a time in this embodiment. With reference to FIG. 31, the words include: words related to a location, words related to food, words related to a name of a person, and the like, in addition to words related to time. Words related to time include, for example, words related to a date and time that is directly referring to time, such as February, July, the 2nd, or 1:00; and words related to a period that is indirectly referring to time such as a school entrance ceremony, graduation ceremony, sports day, or a wedding. Thus, a natural language process classifies temporal words and conducts a cluster analysis of the goal attainment period to identify a goal attainment deadline.

Thus, the control unit 210 identifies and acquires information regarding the deadline for goal attainment from the information input by the user 10 using the information communication terminal 100A and stores the acquired information in the storage unit 220 for each user. When the information regarding the deadline for goal attainment is directly referring to the deadline, the information is used as is, and when the information regarding the deadline for goal attainment is indirectly referring to the deadline, the deadline is estimated.

Returning to FIG. 29, the control unit 210 calculates the gap between the quantitative goal value and information indicating the current self stored in the storage unit 220 (step S124).

Figure 32:
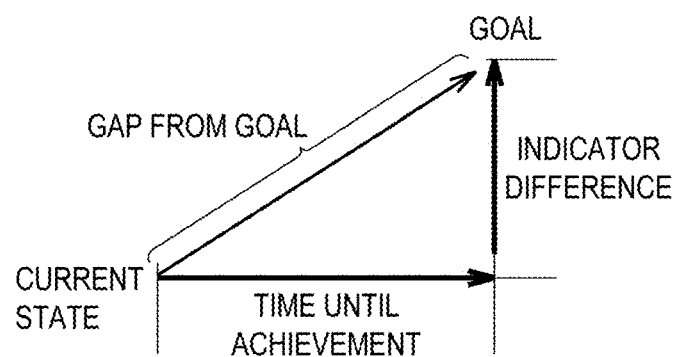
FIG. 32 is a diagram illustrating a gap from a goal value in this embodiment.

FIG. 32 is a diagram illustrating a gap from the goal value in this embodiment. With reference to FIG. 32, the gap from the goal is indicated by the time until achievement and the difference in indicators between the current and goal. In step S124 of FIG. 29, for example, when the current weight and body fat percentage of the user are 65 kg and 30%, respectively, in February, and the goal is a weight of 62 kg and a body fat percentage of 25% by September, the gap is calculated as 7 months for time, −3 kg for weight, and −5% for body fat percentage.

Returning to FIG. 29, the control unit 210 determines whether there is a past usage history of the user 10 of the goal management system on the basis of information stored in the storage 220 and the like (step S125). When it is determined that there is (YES in step S125), the control unit 210 reads information related to the success or failure of the user 10 in goal attainment in the past (step S126).

When it is determined that there is no past usage history of the user 10 (NO in step S125) and after step S126, the control unit 210 reads, of information on a plurality of persons other than the user 10 stored in the storage unit 220, information similar to the current situation of the user 10 (for example, information related to a similar gap from the goal value, information related to a goal similar to that of the user 10, and information related to attributes similar to those of the user 10) (step S127).

Then, the control unit 210 uses the information read in step S126 and step S127 to create a plurality of potential routes to goal attainment (step S128).

Figure 33:
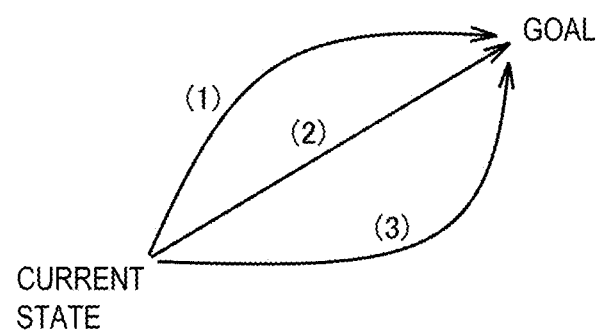
FIG. 33 is a diagram illustrating an example of routes to goal attainment in this embodiment.

FIG. 33 is a diagram illustrating an example of routes to goal attainment in this embodiment. With reference to FIG. 33, the potential routes to goal attainment have a plurality of shapes, such as a straight line like a route (2), a curved line like a route (1) and a route (3), and a stepped shape, and respective rates of change vary in accordance with the gap, time, individual attributes, personality, and the like.

Figure 34:
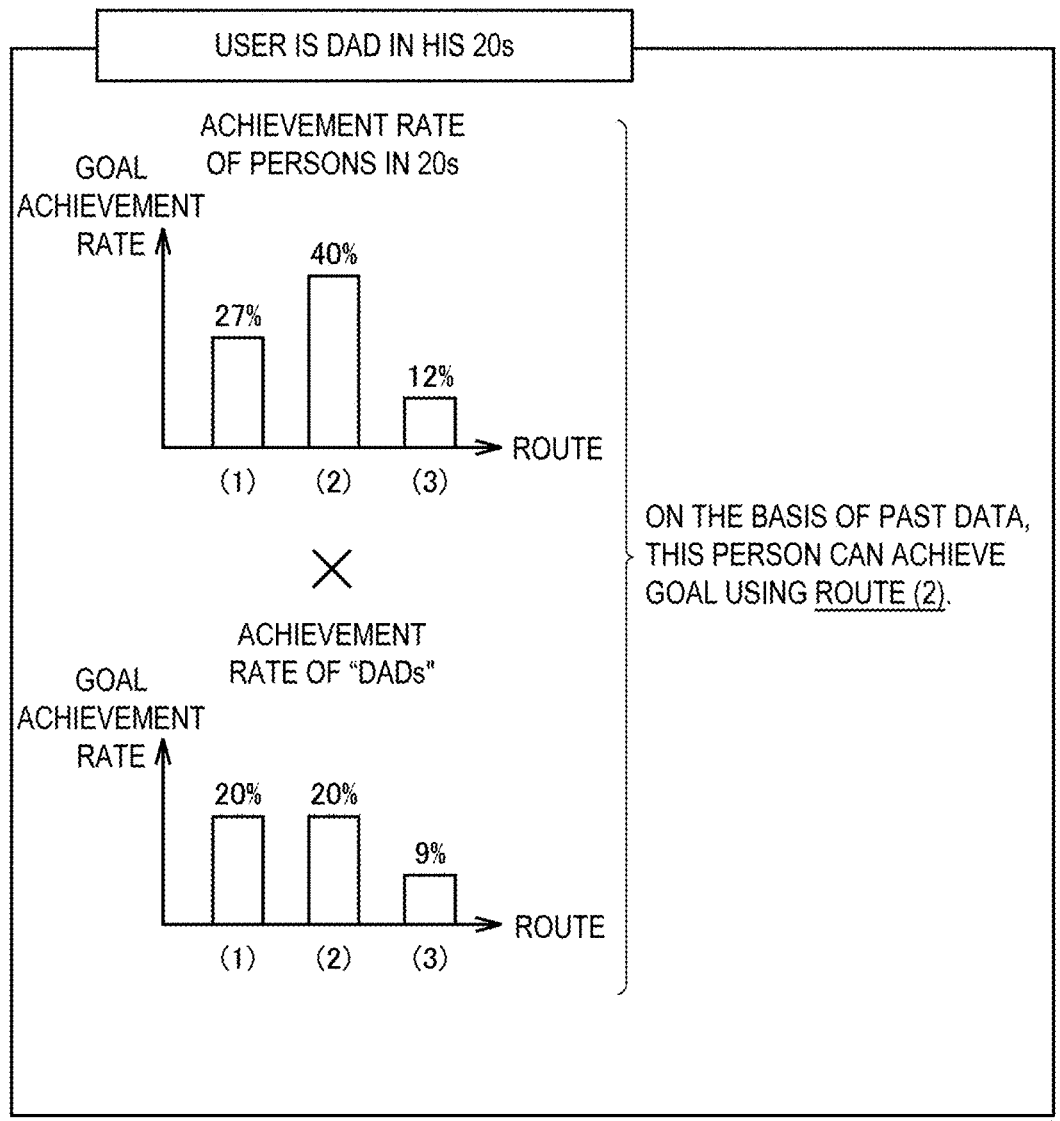
FIG. 34 is a diagram illustrating an example of a process of deciding on recommended routes to goal attainment in this embodiment.

FIG. 34 is a diagram illustrating an example of the process of deciding on the recommended routes to goal attainment in this embodiment. With reference to FIG. 34, in the storage unit 220 of the server 200, the attributes of a plurality of users, the goals related to the bodies of a plurality of users, and information indicating the trends for goal attainment related to the bodies of a plurality of users are associated and accumulated.

For example, information indicating that when the user 10 is "a father in his 20s", the goal achievement rates of other users having the same or a similar goal as that of the user 10 and having the same attribute "20s" as that of the user 10 are 27%, 40%, and 12% for the routes (1) to (3), respectively, and that the goal achievement rates of other users having the same or a similar goal as that of the user 10 and having the same attribute "father" as that of the user 10 are 20%, 20%, and 9% for the routes (1) to (3), respectively, is accumulated. On the basis of this, the route (2) having the highest average value among the average values of the respective goal achievement rates of each route is determined to be the recommended route.

With reference to FIG. 29, the control unit 210 transmits the potential route created in step S128 to the information communication terminal 100A of the user 10 for presentation on the information communication terminal 100A (step S129). The control unit 210 determines whether the user 10 has selected a potential route, that is, whether information indicating a potential route selected from the information communication terminal 100A of the user 10 has been received (step S131).

When a potential route has been selected (YES in step S131), the control unit 210 determines that the route to be used for goal management is the selected potential route (step S132). On the other hand, when a potential route has not been selected (NO in step S131), the control unit 210 determines that the route to be used for goal management is a recommended route such as illustrated in FIG. 34 (step S133).

The control unit 210 transmits the goal route determined in step S132 or step 133 to the information communication terminal 100A of the user 10 for presentation on the information communication terminal 100A (step S134).

Figure 35:
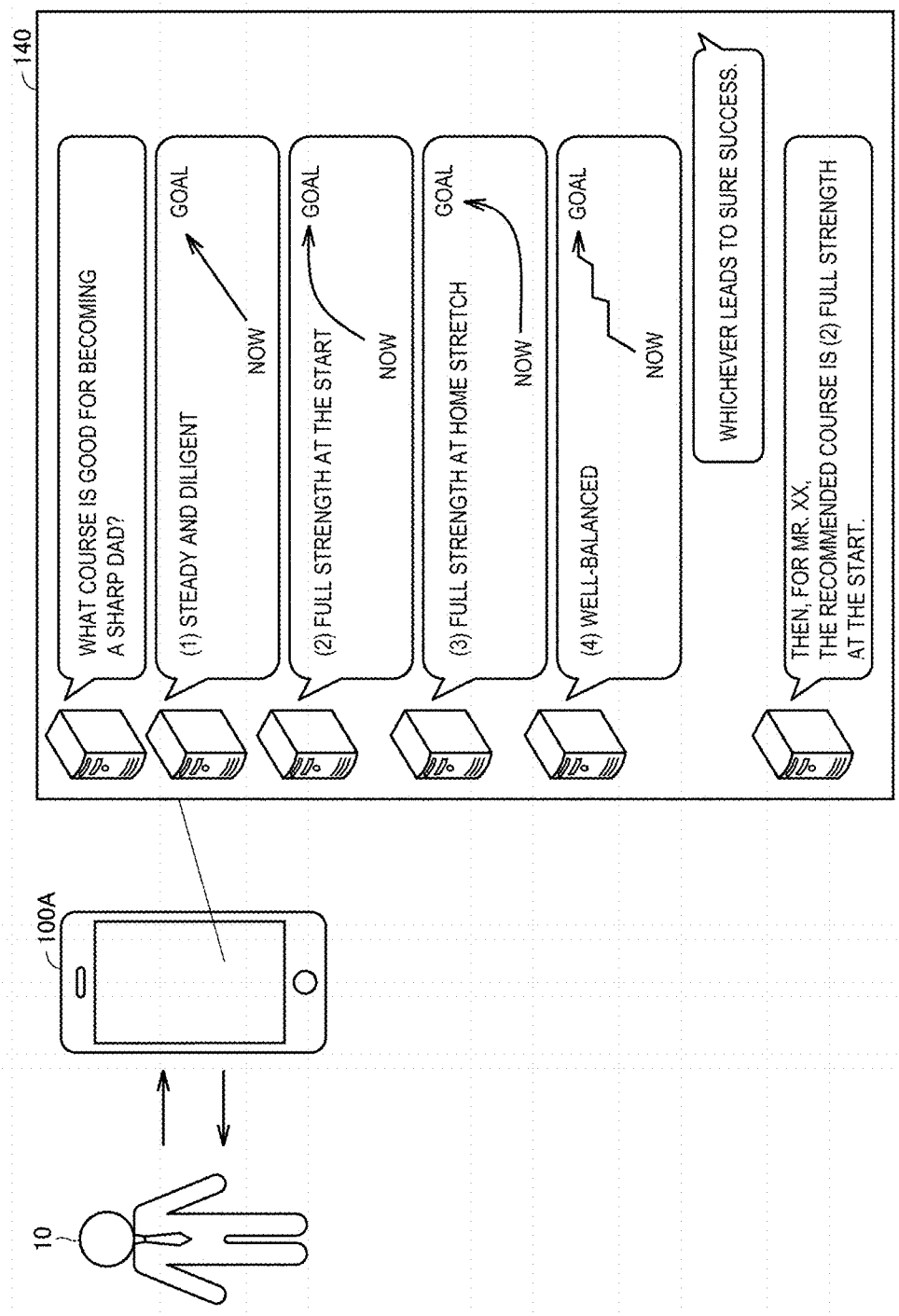
FIG. 35 is a diagram illustrating an example of a display screen displayed on the display unit of the information communication terminal in the goal realization second-half process in this embodiment.

FIG. 35 is a diagram illustrating an example of a display screen displayed on the output unit 140 of the information communication terminal 100A in the goal realization second-half process in this embodiment. With reference to FIG. 35, the five speech balloons from the top are displayed in step S129 of FIG. 29. The sixth and seventh speech balloons from the top are displayed in step S134 of FIG. 29.

Returning to FIG. 29, the control unit 210 selects a goal attainment method (step S135). Specifically, the goal attainment method is selected from the past history and the attributes and preferences of the user 10. For example, for a plurality of users in their 20s, reducing food intake is effective in improving body composition (weight, for example). However, on the basis of information indicating that, according to past history, this user 10 has numerous history logs of walking as a goal attainment method, walking 20 minutes daily is selected as the first recommendation, and reducing food intake is selected as the second recommendation.

Figure 36:
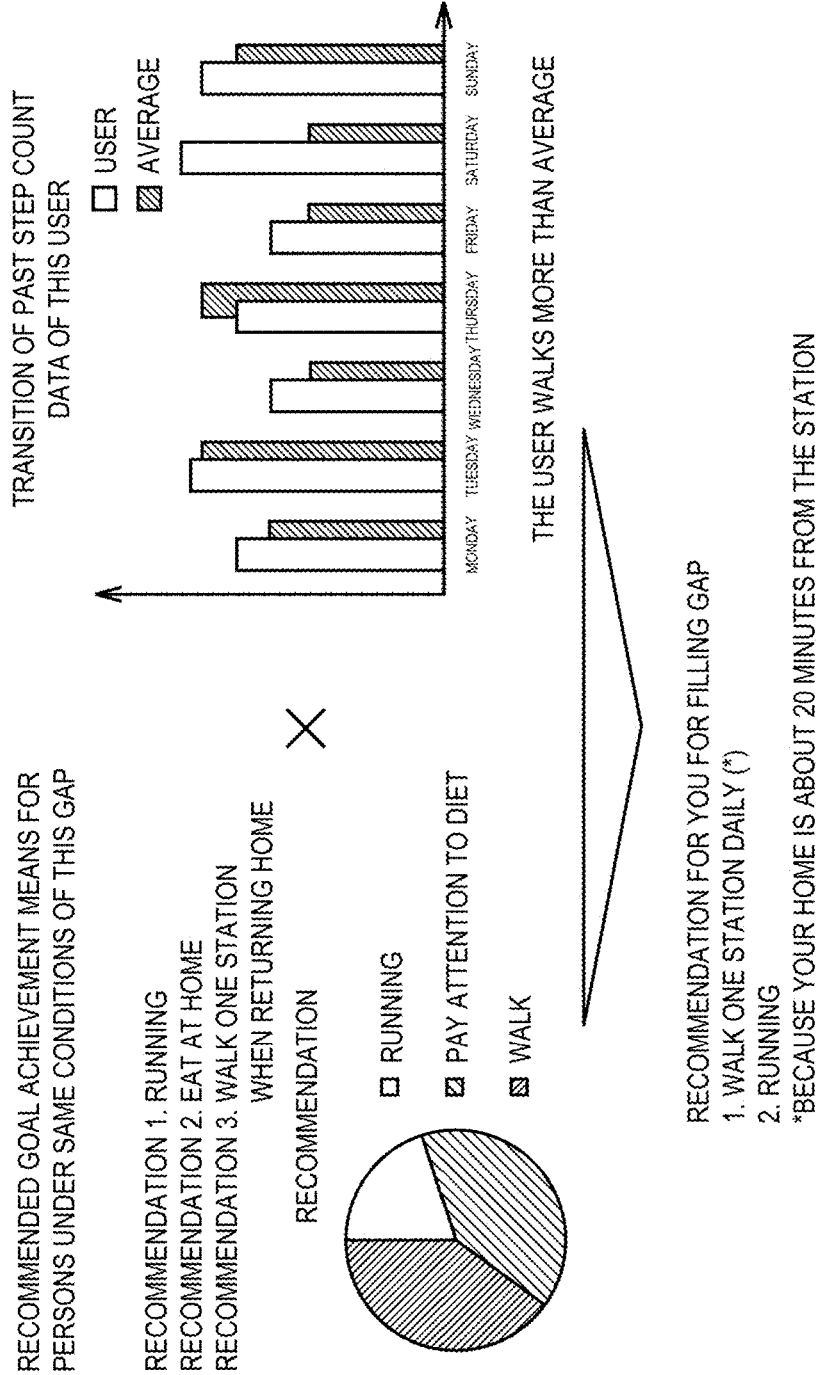
FIG. 36 is a diagram illustrating an example of a process of selecting a goal attainment method in this embodiment.

FIG. 36 is a diagram illustrating an example of the process of selecting the goal attainment method in this embodiment. With reference to FIG. 36, goal attainment means recommended for persons under conditions similar to those of the gap from the goal value of the user 10 are running (first), eating at home (second), and walking from one station when returning home (third).

Further, on the basis of the transition of past step count data of the user 10, the user 10 walks more than the average. Thus, as the goal attainment means recommended to the user 10 for bridging the gap from the goal value, walking from one station per day is selected first since the home of the user 10 is 20 minutes from the station, and running is selected second.

Returning to FIG. 29, the control unit 210 transmits the goal attainment method decided in step S135 to the information communication terminal 100A of the user 10 for presentation on the information communication terminal 100A (step S136). Subsequently, the control unit 210 returns the process to be executed to the calling source of this process.

In the related art, there are systems configured to manage a goal related to a body of a user. In such a system, a message for providing motivation is presented to the user in accordance with a deviation from the path to the goal (refer to, for example, JP 2013-522730 A (hereinafter referred to as "Patent Document 2")). However, in the system of Patent Document 2, the presentation of a path suitable for attainment of a goal related to the body to the user is not considered. In contrast, according to the process illustrated in FIG. 29, it is possible to present a path suitable for attainment of a goal related to the body.

Effect of Embodiments

According to the embodiments described above, effects such as described below can be achieved.

(1-1) In the goal management system, as illustrated in step S111 of FIG. 15, the control unit 110 of the information communication terminal 100A receives input of a qualitative first goal related to the body of the user 10. As illustrated in step S112 to S117, the control unit 210 of the server 200 for goal management identifies a quantitative second goal related to the body of the user 10, from the received first goal. As illustrated in step S118 and FIG. 28, the control unit 110 presents the second goal identified by the server 200.

This makes it possible to indicate a quantitative goal related to the body without receiving input of a goal that is a quantitative numerical value related to the body.

(1-2) As illustrated in step S112 to step S117 of FIG. 15, the control unit 210 converts the first goal into a quantitative goal for at least one of the plurality of feature amounts related to the body to identify the second goal including at least one goal obtained by such conversion. This makes it possible to indicate a quantitative goal for a feature amount related to the body without receiving input of a goal that is a quantitative numerical value related to the body.

(1-3) As illustrated in step S112 to step S117 of FIG. 15, the control unit 210 converts the first goal into a quantitative goal for at least one feature amount corresponding to a meaning obtained by linguistic analysis of the first goal. This makes it possible to indicate a quantitative goal for a feature amount corresponding to the meaning of the first goal.

(1-4) As illustrated in step S112 to step S117 of FIG. 15, the quantitative goal is a range or a value included in a range of values of a feature amount corresponding to a meaning obtained by linguistic analysis of the first goal. This makes it possible to indicate a quantitative goal for a feature amount corresponding to the meaning of the first goal.

(1-5) When there are a plurality of meanings obtained by linguistic analysis of the first goal, the quantitative goal is a range or a value included in a range of values of a feature amount per meaning. This makes it possible to indicate a quantitative goal for a plurality of feature amounts corresponding to the meaning of the first goal.

(1-6) As illustrated in step S112 to step S117 of FIG. 15, when there are a plurality of feature amounts corresponding to a meaning obtained by linguistic analysis of the first goal and there is an overlap in range of the plurality of feature amounts per meaning in a multidimensional space with each of the plurality of feature amounts serving as an axis, the quantitative goal is a value or a range of each feature amount corresponding to a position or a range of a multidimensional space included in the overlapping range. This makes it possible to indicate a quantitative goal that fully satisfies a plurality of feature amounts corresponding to the meaning of the first goal.

(2-1) As illustrated in step S121 and step S122 of FIG. 29, in the goal management system, the control unit 110 of the information communication terminal 100A acquires a current value of the predetermined indicator related to the body of the user 10, the goal value, and the achievement deadline of the goal. As illustrated in step S127 and FIG. 34, the storage unit 220 of the server 200 for goal management is configured to store in advance, in association with a plurality of human attributes, information indicating a trend in goal attainment that is indicated by a combination of a plurality of paths, each path being a transition in value of the predetermined indicator to a goal value for achieving a goal related to a body of a person, and a goal attainment rate per path. As illustrated in step S123 to step S128, the control unit 210 of the server 200 is configured to create a path having the goal attainment rate higher than those of other paths on the basis of the current value, the goal value, and the achievement deadline thus acquired, using a trend indicated by information stored in the storage unit 220. As illustrated in step S129 and FIG. 35, the control unit 110 presents the path created by the server 200. This makes it possible to present a path suitable for attainment of a goal related to the body.

(2-2) As illustrated in FIG. 34, the storage unit 220 is configured to further store a plurality of past goals, each related to a body of a person, in association with the trend. As illustrated in step S123 to step S128 of FIG. 29, the control unit 210 is configured to create the path using a trend indicated by, from among the information stored in the storage unit, information of each person having a goal at or near that of the user 10. This makes it possible to present a path suitable for attainment of a goal related to the body on the basis of the information of other users.

(2-3) As illustrated in step S123 to step S128 of FIG. 29, the control unit 210 is configured to create the path using a trend indicated by, from among the information stored in the storage unit 220, information of each person having an attribute at or near that of the user 10. This makes it possible to present a path suitable for attainment of a goal related to the body on the basis of the information of other users.

(2-4) As illustrated in FIG. 34, the storage unit 220 is configured to store an achievement rate of a goal as the trend. As illustrated in step S123 to step S128 of FIG. 29, the server 210 is configured to create the path using an achievement rate indicated by, from among the information stored in the storage unit 220, information of each person having an attribute at or near that of the user 10. This makes it possible to present a path suitable for attainment of a goal related to the body on the basis of the information of other users.

Modified Examples (1) In the embodiments described above, the disclosure of the goal management system has been described. However, the disclosure is not limited thereto and can be regarded as the server 200 and the information communication terminal 100 for goal management included in the goal management system. Further, the disclosure can be regarded as a non-transitory computer-readable storage medium storing a program and a method for goal management executed on the server 200 and the information communication terminal 100.

Further, the invention can also be regarded as a computer-readable recording medium in which the program is recorded. This recording medium may be a magnetic tape, a flexible disk, a magnetic disk such as a hard disk, an optical disk such as a CD-ROM, a CD-R, a CD-RW, a DVD-ROM, a DVD-R, a DVD-RW, a DVD-RAM, a DVD+R, or a DVD+RW, a magneto-optical disk such as an MO, or a memory card. Alternatively, the recording medium may be a medium that holds a program in a fixed manner, such as a USB memory or may be a medium that holds a program in a dynamic manner that allows the program to be downloaded via a communication network from a server such as an application service provider (ASP).

(2) In the embodiment described above, the server 200 for goal management is a single computer. However, the server 200 is not limited thereto and may be a server group composed of a plurality of computers.

(3) In the embodiment described above, the functions executed by the goal management system are realized by software composed of the program processes described in FIG. 14, FIG. 15, and FIG. 29 being executed by the CPU of the control unit 210. However, realization is not limited thereto, and a portion or all of these functions may be configured to be realized by dedicated hardware.

(4) In the embodiment described above, a portion of the functions executed on the server 200 may be executed on the information communication terminal 100. For example, when the control unit 210 of the server 200 identifies a predetermined value using the predetermined data stored in the storage unit 220 and transmits the identified predetermined value to the information communication terminal 100, the control unit 210 of the server 200 may transmit the predetermined data stored in the storage unit 220 to the information communication terminal 100. Then, the predetermined value may be identified using the predetermined data received by the control unit 110 of the information communication terminal 100.

(5) The techniques described in the embodiments and modified examples are intended to be practiced alone or in combination to the extent possible.

The embodiments disclosed herein are illustrative in all respects and are not intended as limitations. The scope of the present disclosure is indicated not by the descriptions of embodiments above but by the claims and includes all meaning equivalent to the scope and changes within the scope.

REFERENCE SIGNS LIST

10, 20, 30 User
100, 100A, 100B, 100C Information communication terminal
110, 210, 510 Control unit
120, 220, 520 Storage unit
130, 530 Operation unit
140, 540 Output unit
150, 250 External storage device
151, 251 Recording medium
160, 170, 570 Wireless communication unit
200, 300 Server
260 Communication unit
500 Measuring device
580 Measuring unit
800, 800A, 800B Communication equipment
900 Communication network

The invention claimed is:

1. A goal management system comprising:
a reception unit configured to receive input of a first goal that is qualitative and related to a body of a user;
an identification unit configured to identify a second goal that is quantitative and related to the body of the user, from the first goal received by the reception unit, the identification unit being configured to convert the first goal into a quantitative goal for at least one feature amount related to the body and corresponding to a meaning obtained by linguistic analysis of the first goal, thereby identifying the second goal including at least one goal obtained by such conversion; and
a presentation unit configured to present the second goal identified by the identification unit,
the goal management system further comprising:
an acquisition unit configured to acquire a current value of a predetermined indicator related to the body of the user and to acquire an achievement deadline of a goal;
a storage unit configured to store in advance, in association with a plurality of human attributes, information indicating a trend in goal attainment that is indicated by a combination of a plurality of paths, each path being a transition in value of the predetermined indicator to a goal value for achieving a goal related to a body of a person, and a goal attainment rate per path;
a creation unit configured to create a path having the goal attainment rate higher than those of other paths on the basis of the current value, the second goal, and the achievement deadline, using a trend indicated by information stored in the storage unit; and
a presentation unit configured to present the path created by the creation unit, wherein
the storage unit is configured to further store a plurality of past goals, each related to a body of a person, in association with the trend, and
the creation unit is configured to create the path using a trend indicated by, from among the information stored in the storage unit, information of each person having a goal at or near that of the user.

2. A goal management system comprising:
a reception unit configured to receive input of a first goal that is qualitative and related to a body of a user;
an identification unit configured to identify a second goal that is quantitative and related to the body of the user, from the first goal received by the reception unit, the identification unit being configured to convert the first goal into a quantitative goal for at least one feature amount related to the body and corresponding to a meaning obtained by linguistic analysis of the first goal, thereby identifying the second goal including at least one goal obtained by such conversion; and
a presentation unit configured to present the second goal identified by the identification unit,
the goal management system further comprising:
an acquisition unit configured to acquire a current value of a predetermined indicator related to the body of the user and to acquire an achievement deadline of a goal;
a storage unit configured to store in advance, in association with a plurality of human attributes, information indicating a trend in goal attainment that is indicated by a combination of a plurality of paths, each path being a transition in value of the predetermined indicator to a goal value for achieving a goal related to a body of a person, and a goal attainment rate per path;
a creation unit configured to create a path having the goal attainment rate higher than those of other paths on the basis of the current value, the second goal, and the achievement deadline, using a trend indicated by information stored in the storage unit; and
a presentation unit configured to present the path created by the creation unit,
wherein the creation unit is configured to create the path using a trend indicated by, from among the information stored in the storage unit, information of each person having an attribute at or near that of the user.

3. A non-transitory computer-readable storage medium storing a goal management program executed by a control unit of a server including the control unit and a storage unit, the storage unit being configured to store in advance a plurality of types of feature amounts, the control unit executing the goal management program comprising the steps of:

receiving a first goal that is qualitative, related to a body of a user, and received by a terminal device;

identifying a second goal that is quantitative and related to the body of the user from the first goal thus received; and transmitting the second goal thus identified to the terminal device for presentation by the terminal device, the storage unit being configured to further store in advance, in association with a plurality of human attributes, information indicating a trend in goal attainment that is indicated by a combination of a plurality of paths, each path being a transition in value of a predetermined indicator to a goal value for achieving a goal related to a body of a person, and a goal attainment rate per path, the control unit executing the goal management program further comprising the steps of:

acquiring a current value of the predetermined indicator related to the body of the user, the goal value, and an achievement deadline of the goal;

creating a path having the goal attainment rate higher than those of other paths from the current value, the goal value, and the achievement deadline thus acquired, using a trend indicated by information stored in the storage unit; and transmitting the path thus created to the terminal device for presentation by the terminal device, wherein the storage unit is configured to further store a plurality of past goals, each related to a body of a person, in association with the trend, and the creation unit is configured to create the path using a trend indicated by, from among the information stored in the storage unit, information of each person having a goal at or near that of the user.

4. A non-transitory computer-readable storage medium storing a goal management program executed by a control unit of a server including the control unit and a storage unit, the storage unit being configured to store in advance a plurality of types of feature amounts, the control unit executing the goal management program comprising the steps of:

receiving a first goal that is qualitative, related to a body of a user, and received by a terminal device;

identifying a second goal that is quantitative and related to the body of the user from the first goal thus received; and transmitting the second goal thus identified to the terminal device for presentation by the terminal device, the storage unit being configured to further store in advance, in association with a plurality of human attributes, information indicating a trend in goal attainment that is indicated by a combination of a plurality of paths, each path being a transition in value of a predetermined indicator to a goal value for achieving a goal related to a body of a person, and a goal attainment rate per path, the control unit executing the goal management program further comprising the steps of:

acquiring a current value of the predetermined indicator related to the body of the user, the goal value, and an achievement deadline of the goal;

creating a path having the goal attainment rate higher than those of other paths from the current value, the goal value, and the achievement deadline thus acquired, using a trend indicated by information stored in the storage unit; and transmitting the path thus created to the terminal device for presentation by the terminal device, wherein the creation unit is configured to create the path using a trend indicated by, from among the information stored in the storage unit, information of each person having an attribute at or near that of the user.

* * * * *